United States Patent [19]

Stout et al.

[11] Patent Number: 6,051,399
[45] Date of Patent: Apr. 18, 2000

[54] PRODUCTION OF C-TERMINAL AMIDATED PEPTIDES FROM RECOMBINANT PROTEIN CONSTRUCTS

[75] Inventors: Jay S. Stout; Bruce E. Partridge; Dennis B. Henriksen; Barton Holmquist, all of Lincoln; Fred W. Wagner, Walton, all of Nebr.

[73] Assignee: BioNebraska, Inc., Lincoln, Nebr.

[21] Appl. No.: 08/934,171

[22] Filed: Sep. 19, 1997

Related U.S. Application Data

[63] Continuation of application No. 08/350,528, Dec. 7, 1994, abandoned.

[51] Int. Cl.$^7$ ............................ C12P 21/00; C07K 14/46; C07H 21/04
[52] U.S. Cl. .................. 435/69.1; 435/68.1; 435/69.4; 435/69.7; 435/69.8; 530/308; 530/324; 530/345; 536/23.4
[58] Field of Search ..................... 435/68.1, 69.1, 435/69.4, 69.7, 69.8; 530/308, 324, 345; 536/23.4

[56] References Cited

U.S. PATENT DOCUMENTS

| | | | |
|---|---|---|---|
| 4,339,534 | 7/1982 | Johansen et al. | 435/68.1 |
| 4,431,739 | 2/1984 | Riggs | 435/252.33 |
| 4,543,329 | 9/1985 | Daum et al. | 435/69.1 |
| 4,703,004 | 10/1987 | Hopp et al. | 435/69.7 |
| 4,709,014 | 11/1987 | Tamaoki | 530/333 |
| 4,769,326 | 9/1988 | Rutter | 435/68.1 |
| 4,782,137 | 11/1988 | Hopp et al. | 530/328 |
| 4,801,536 | 1/1989 | Stahl et al. | 435/69.1 |
| 4,806,473 | 2/1989 | Johansen et al. | 435/68.1 |
| 4,816,397 | 3/1989 | Boss et al. | 435/69.6 |
| 5,004,686 | 4/1991 | Cohen et al. | 435/69.1 |
| 5,013,653 | 5/1991 | Huston et al. | 435/69.7 |
| 5,093,241 | 3/1992 | Bennett et al. | 435/69.4 |
| 5,166,321 | 11/1992 | Lai et al. | 530/324 |
| 5,168,049 | 12/1992 | Meade et al. | 435/69.1 |
| 5,279,954 | 1/1994 | Wagner et al. | 435/176 |
| 5,512,459 | 4/1996 | Wagner et al. | 435/68.1 |
| 5,595,887 | 1/1997 | Coolidge et al. | 435/69.7 |

FOREIGN PATENT DOCUMENTS

| | | |
|---|---|---|
| 0017485 | 10/1980 | European Pat. Off. . |
| 0131363 | 1/1985 | European Pat. Off. . |
| 0163406 | 12/1985 | European Pat. Off. . |
| 197794 | 10/1986 | European Pat. Off. . |
| 0286239 | 10/1988 | European Pat. Off. . |
| 0301485 | 2/1989 | European Pat. Off. . |
| 307860 | 3/1989 | European Pat. Off. . |
| 308067 | 3/1989 | European Pat. Off. . |
| 0333691 | 9/1989 | European Pat. Off. . |
| 0401657 | 12/1990 | European Pat. Off. . |
| 0499990 | 8/1992 | European Pat. Off. . |
| 499990 | 8/1992 | European Pat. Off. . |
| 0528271 | 2/1993 | European Pat. Off. . |
| 528 686 | 2/1993 | European Pat. Off. . |
| 561412 | 9/1993 | European Pat. Off. . |
| 3523701 | 1/1987 | Germany . |
| 2180539 | 4/1987 | United Kingdom . |
| 2246133 | 1/1992 | United Kingdom . |
| 88/02406 | 4/1988 | WIPO . |
| 88/07086 | 9/1988 | WIPO . |
| WO 88/07085 | 9/1988 | WIPO . |
| WO 90/08194 | 7/1990 | WIPO . |
| WO 92/00993 | 1/1992 | WIPO . |
| 92/01707 | 2/1992 | WIPO . |
| WO 92/01707 | 2/1992 | WIPO . |
| 93/25579 | 12/1993 | WIPO . |

OTHER PUBLICATIONS

Van Heeke, et al., *Protein Expression and Purification*, 4, pp. 265–274 (1993).
Büllesbach et al., *Biochem.*, 25, 5998–6004 (1986).
Engels, et al., *Protein Engineering*, 1, pp. 195–199 (1987).
Mortensen, et al., *Biochemistry*, 33, pp. 508–517, (1994).
Breddam et al. Carlsberg Res. Commun., 45:237–247 (1980).
Mortensen et al. J. Am. Chem. Soc., 116:34–41 (1994).
Aasmul–Olsen et al. Carboxypeptidase mediated C–terminal amidation of polypeptide acids. Biomedica Biochimica Acta. vol. 50, Nos. 10/11, pp. S 106–S 109, 1991.
K. Breddam et al., "Carboxypeptidase Y Catalyzed Transpeptidations and Enzymatic Peptide Synthesis", *Carlsberg Res. Commun.*, 45:237–247 (1980).
K. Breddam et al., "Carboxypeptidase Y Catalyzed C–Terminal Modifications of Peptides", *Carlsberg Res. Commun.*, 46:121–128 (1981).
K. Breddam et al., "Carboxypeptidase Y Catalyzed C–Terminal Modification in the B–Chain of Porcine Insulin", *Carlsberg Res. Commun.*, 46:361–371 (1981).
K. Breddam et al., "Isolation of Carboxypeptidase from Malted Barley by Affinity Chromatography", *Carlsberg Res. Commun.*, 48:217–230 (1983).
K. Breddam et al., "Carboxypeptidase Y Catalyzed Transpeptidation and Condensation Reactions", *Carlsberg Res. Commun.*, 49:457–462 (1984).
K. Breddam et al., "Malt Carboxypeptidase Catalyzed Aminolysis Reactions", *Carlsberg Res. Commun.*, 49:473–481 (1984).
K. Breddam, "Isolation of Carboxypeptidase II from Malted Barley by Affinity Chromatography", *Carlsberg Res. Commun.*, 50:199–209 (1985).
K. Breddam, "Enzymatic Properties of Malt Carboxypeptidase II in Hydrolysis and Aminolysis Reacations", *Carlsberg Res. Commun.*, 50:309–323 (1985).

(List continued on next page.)

*Primary Examiner*—Elizabeth Kemmerer
*Assistant Examiner*—David Romeo
*Attorney, Agent, or Firm*—Foley & Lardner

[57] ABSTRACT

A method for the production of C-terminal amidated recombinant peptides is provided. The method employs a recombinant protein construct having multiple copies of a target peptide linked by intraconnecting peptides. The intraconnecting peptides permit the multicopy construct to be selectively reacted to produce product peptides having a C-terminal α-carboxamide. A recombinant gene containing a DNA sequence coding for the recombinant protein construct and an expression cassette, an expression vector and a transformed cell including the recombinant gene are also provided.

13 Claims, 9 Drawing Sheets

OTHER PUBLICATIONS

K. Breddam et al., "Primary Structure and Enzymatic Properties of Carboxypeptidase II from Wheat Bran", *Carlsberg Rec. Commun.*, 52:297–311 (1987).

K. Breddam, "Serine Carboxypeptidases. A Review.", *Carlsberg Res. Commun.*, 51:83–128 (1986).

K. Breddam, Carboxypeptidase S–1 From Penicillium Janthinellum: Enzymatic Properties in Hydrolysis and Aminolysis Reactions, *Carlsberg Res. Commun.*, 53:309–320 (1988).

J. Johansen et al., "Isolation of Carboxypeptidase Y By Affinity Chromatography", *Carlsberg Res. Commun.*, 41:1–14 (1976).

Y. Kubota et al., "Carboxypeptidase $C_N$", *J. Biochem.*, 74:757–770 (1973).

U. Mortensen et al., "Site–Directed Mutagenesis on (Serine) Carboxypeptidase Y", *Biochem.*, 33:508–517 (1994).

F. Widmer et al., "Influence of the Structure of Amine Components on Carboxypeptidase Y Catalyzed Amide Bond Formation", *Carlsberg Res. Commun.*, 46:97–106 (1981).

J. Winther et al., "Increased Hydrophobicity of the $S_1$ Binding Site in Carboxypeptidase Y Obtained by Site–Directed Mutagenesis", *Carlsberg Res. Commun.*, 50:273–284 (1985).

Schellenberger, et al., *Biochemistry*, 32:4349 (1993).

Bech, et al., *Carlsberg Res. Comm.*, 53, pp. 381–393 (1988).

Bongers, et al., *Biomed. Biochim. Acta*, 50 pp. 157–162, (1991).

Bongers, et al., *Int. J. Peptide Protein Res.*, 40 pp. 268–273, 1992).

Bradbury, et al., *Biochem. & Biophys. Res. Com.*, 154, pp. 1293–1300 (1988).

Breddam, et al., *Int. J. Peptide Protein Res.*, 37, pp. 153–160, (1991).

Breddam, et al., *Carlsberg Res. Comm.*, 49, pp. 463–472 (1984).

Breddam, *Carlsberg Res. Comm.*, 49, pp. 535–554 (1984).

Carles, et al., *Federation of European Biochemical Societies*, 212, pp. 163–167, (1987).

Carter, *American Chemical Society Symposium Series*, 13, pp. 181–193 (1990).

Endrizzi, et al., *Biochemistry*, 33, pp. 11106–11120, (1994).

Ford, et al., *Protein Expression and Purification*, 2, pp. 95–107 (1991).

Fruton, in *Advances in Enzymology*, (vol. 53, A. Meister, ed. John Wilry and Sons, New York), pp. 239–306, (1982).

Germino, et al., *Proc. Natl. Acad. Sci. USA*, 81, pp. 4692–4696, (1984).

Gutniak, et al., *New Eng. J. Med.*, 326, pp. 1316–1322, (1992).

Hammarberg, et al., *Proc. Natl. Acad. Sci. USA*, 86, pp. 4367–4371 (1989).

Hanada, et al., *J. Bio. Chem.*, 263, pp. 7181–7185 (1988).

Hartley, et al., *Gene*, 13, pp. 347–353 (1981).

Henriksen, et al., *J. Am. Chem. Soc.*, 114, pp. 1876–1877, (1992).

Hopp, et al., *Bio/Technology*, 6, pp. 1204–1210 (1988).

Huse, et al., *Science*, 246, pp. 1275–1281, (1989).

Itakura, et al., *Science*, 198, pp. 1056–1063 (1977).

Johansen, *Carlsberg Res. Commun.*, 41, pp. 73–80, (1976).

Kempe, et al., *Gene*, 39, pp. 239–245, (1985).

Kempe, et al., *Bio/Technology*, 4, pp. 565–568, (1986).

Kirschner, et al., *Journal of Biotechnology*, 12, pp. 247–260, (1989).

Koyama, et al., *Journal of Biotechnology*, 32, pp. 273–281, (1994).

Ladisch, et al., published 1990 by *American Chemical Society* (Washington, D.C.), pp. 181–193 (1990).

Marston, *Biochem. J.*, 240, pp. 1–12 (1986).

Moks, et al., *Biochemistry*, 26, pp. 5239–5244 (1987).

Morihara, *Tibtech*, 5, pp. 164–170, (1987).

Nakagawa, et al., *J. Am. Chem. Soc.*, 116, pp. 5513–5514, (1994).

Niall, et al., *Proc. Natl. Acad. Sci. USA*, 64, pp. 771–778 (1969).

Ohsuye, et al., *Biochemical and Biophysical Research Communications*, 150, pp. 1275–1281 (1988).

Oldenburg, et al., *Protein Expression and Purification*, 5, pp. 278–284, (1994).

Olesen, et al., *Protein Engineering*, 6, pp. 409–415 (1993).

Sakina et al., *Chem. Pharm. Bull.*, 36, pp. 4345–4354 (1988).

Sakina et al., *Chem. Pharm. Bull.*, 37, pp. 811–812 (1989).

Sassenfeld, *Tibtech*, 8, pp. 89–93 (1990).

Schellenberger, et al., *Int. J. Peptide Protein Res.*, 39, pp. 472–476, (1992).

Schellenberger, et al., *Int. J. Peptide Protein Res.*, 41, pp. 326–332, (1993).

Scopes, et al., *Protein Purification: Principles in Practice*, (vol. 3, Springer–Verlag, New York), pp. 41–71, (1987).

Shen, *Proc. Natl. Acad. Sci. USA*, 81, pp. 4627–4631, (1984).

Spande, et al., *Laboratory of Chemistry, Natl Institute of Arthritis and* Metabolic Diseases, Natl Institutes of Health, Bethesda, Maryland, pp. 97–125 (1970).

Tajima, et al., *Journal of Fermentation and Bioengineering*, 72, pp. 362–367 (1991).

Tanhauser et al., *Gene*, 117, pp. 113–117 (1992).

Uhlen, et al., *Methods in Enzymology*, 185, pp. 129–143 (1990).

Ward et al., *Nature*, 341, pp. 544–546 (1989).

Yoo, et al., *J. Bio. Chem.*, 264 pp. 17078–17083 (1989).

FIG. 1

```
-hCA                                                                           THROMBIN  PTH(1-
     Ile  Lys  Ala  Ser  Ala  Met  Gly  Gly  Arg  Val  Asp  Arg  Gly  Pro  Arg  Ser  Val  Ser
     ATC  AAA  GCT  TCT  GCC  ATG  GGC  GGC  CGC  GTC  GAC  CGT  GGT  CCG  CGT  TCT  GTT  TCT
     TAG  TTT  CGA  AGA  CGG  TAC  CCG  CCG  GCG  CAG  CTG  GCA  CCA  GGC  GCA  AGA  CAA  AGA
          Hind III            Nco I           NotI          Sal I Glu  Ile  Gln  Leu  Met  His  Asn  Leu  Gly  Lys  His  Leu  Asn  Ser  Met  Glu  Arg  Val
     GAA  ATC  CAG  CTG  ATG  CAC  AAC  CTG  GGT  AAA  CAC  CTG  AAC  TCT  ATG  GAA  CGT  GTT
     CTT  TAG  GTC  GAC  TAC  GTG  TTG  GAC  CCA  TTT  GTG  GAC  TTG  AGA  TAC  CTT  GCA  CAA 34) CYS
     Glu  Trp  Leu  Arg  Lys  Lys  Leu  Gln  Asp  Val  His  Asn  Phe  Cys  Ala  Leu  Glu  Stop
     GAA  TGG  CTG  CGT  AAA  AAA  CTG  CAG  GAC  GTT  CAC  AAC  TTC  TGC  GCT  CTC  GAG  TAA  GAT  ATC
     CTT  ACC  GAC  GCA  TTT  TTT  GAC  GTC  CTG  CAA  GTG  TTG  AAG  ACG  CGA  GAG  CTC  ATT  CTA  TAG
                                      Pst I                           Xho I         EcoR V
```

FIG. 2

```
-hCA                                                              THROMBIN    PTH(1-
 Ile Lys Ala Ser Ala Met Gly Gly Arg Val Asp Arg Gly Pro Arg Ser Val Ser
 ATC AAA GCT TCT GCC ATG GGC GGC CGC GTC GAC CGT GGT CCG CGT TCT GTT TCT
 TAG TTT CGA AGA CGG TAC CCG CCG GCG CAG CTG GCA CCA GGC GCA AGA CAA AGA
        Hind III          Nco I       NotI       Sal I Glu Ile Gln Leu Met His Asn Leu Gly Lys His Leu Asn Ser Met Glu Arg Val
 GAA ATC CAG CTG ATG CAC AAC CTG GGT AAA CAC CTG AAC TCT ATG GAA CGT GTT
 CTT TAG GTC GAC TAC GTG TTG GAC CCA TTT GTG GAC TTG AGA TAC CTT GCA CAA Glu Trp Leu Arg Lys Lys Leu Gln Asp Val His Asn Phe Cys Ala Leu Asp Ser
 GAA TGG CTG CGT AAA AAA CTG CAG GAC GTT CAC AAC TTC TGC GCT CTC GAC TCT
 CTT ACC GAC GCA TTT TTT GAC GTC CTG CAA GTG TTG AAG CGA GAG CTG AGA AGA
                              Pst I                34)  CYS THROMBIN  PTH(1-
 Pro Arg Ser Val Ser Glu Ile Gln Leu Met His Asn Leu Gly Lys His Leu Asn
 CCG CGT TCT GTT TCT GAA ATC CAG CTG ATG CAC AAC CTG GGT AAA CAC CTG AAC
 GGC GCA AGA CAA AGA CTT TAG GTC GAC TAC GTG TTG GAC CCA TTT GTG GAC TTG Ser Met Glu Arg Val Glu Trp Leu Arg Lys Lys Leu Gln Asp Val His Asn
 TCT ATG GAA CGT GTT GAA TGG CTG CGT AAA AAA CTG CAG GAC GTG CAC AAC
 AGA TAC CTT GCA CAA CTT ACC GAC GCA TTT TTT GAC GTC CTG CAC GTG TTG
                                                    Pst I 34) CYS
 Phe Cys Ala Leu Glu Stop
 TTC TGC GCT CTC GAG TAA GAT ATC
 AAG ACG CGA GAG CTC ATT CTA TAG
          Xho I                EcoR V
```

FIG. 3

```
        -hCA                                                  THROMBIN                        CYS                                   ENTERO-
        Lys  Ala  Phe  Gly  Gly  Gly  Gly  Pro  Arg  Gly      Cys  Ala  Met  Val  Asp  Asp  Asp
        AAA  GCT  TTC  GGT  GGT  GGT  GGT  CCG  CGT  GGT      TGC  GCC  ATG  GTC  GAC  GAC  GAC
        TTT  CGA  AAG  CCA  CCA  CCA  CCA  GGC  GCA  CCA      ACG  CGG  TAC  CAG  CTG  CTG  CTG
             HindIII                                                    (NcoI)    SalI KINASE  GRF
                 1    2    3    4    5*   6    7    8    9    10   11   12   13*  14*  15   16
                Tyr  Ala  Asp  Ala  Ile  Phe  Thr  Asn  Ser  Tyr  Arg  Lys  Val  Leu  Gly  Gln
                TAC  GCT  GAC  GCT  ATC  TTC  ACC  AAC  TCT  TAC  CGT  AAA  GTT  CTG  GGT  CAG
                ATG  CGA  CTG  CGA  TAG  AAG  TGG  TTG  AGA  ATG  GCA  TTT  CAA  GAC  CCA  GTC
                                         (SspI)                                      (AvrII)    PvuII 17   18   19   20   21   22   23   24   25   26   27   28*  29*  30   31   32   33   34
        Leu  Ser  Ala  Arg  Lys  Leu  Leu  Gln  Asp  Ile  Met  Ser  Arg  Gln  Gln  Gly  Glu  Ser
        CTG  TCT  GCT  CGT  AAA  CTG  CTG  CAG  GAC  ATC  ATG  TCC  CGT  CAG  CAG  GGT  GAA  TCT
        GAC  AGA  CGA  GCA  TTT  GAC  GAC  GTC  CTG  TAG  TAC  AGG  GCA  GTC  GTC  CCA  CTT  AGA
                                              PstI                        (SalI)

35   36   37   38   39*  40   41   42   43   44   CYS
        Asn  Gln  Glu  Arg  Gly  Ala  Arg  Ala  Arg  Leu  Cys  Ala  Met  Leu  Glu  Stop
        AAC  CAG  GAA  CGT  GGT  GCT  CGT  GCT  CGT  CTG  TGC  GCT  ATG  CTC  GAG  TAA
        TTG  GTC  CTT  GCA  CCA  CGA  GCA  CGA  GCA  GAC  ACG  CGA  TAC  GAG  CTC  ATT
                              (SacI)                                        XhoI GAT  ATC  GAA  TTC  GG
        CTA  TAG  CTT  AAG  CC
        EcoRV     EcoRI
```

FIG. 4A

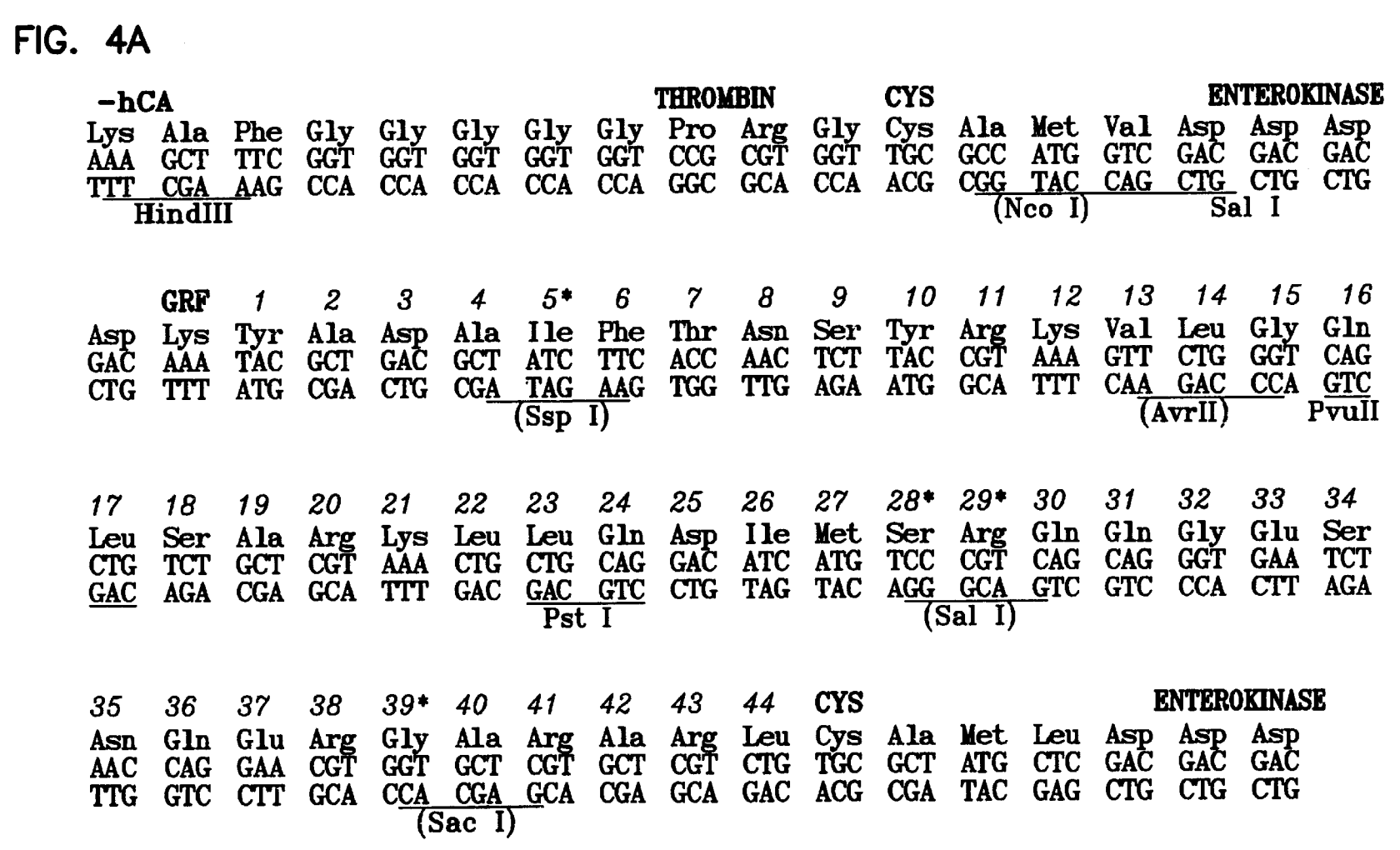

```
-hCA
     Lys Ala Phe
     AAA GCT TTC
     TTT CGA AAG
         HindIII

GRF  1   2   3   4   5*  6   7   8        THROMBIN    9   10       CYS
          Tyr Gly Ala Asp Ala Ile Phe Gly Gly Pro Arg      Gly Cys
          TAC GGT GCT GAC GCT ATC TTC GGT GGT CCG CGT      GGT TGC
          ATG CCA CGA CTG CGA TAG AAG CCA CCA GGC GCA      CCA ACG
                                      (Ssp I)

Ala Met Val Asp Asp Asp
         GCC ATG GTC GAC GAC GAC
         CGG TAC CAG CTG CTG CTG
         (Nco I)   Sal I       ENTEROKINASE 17  18  19  20  21  22  23  24  25  26  27  28* 29* 30  31  32  33  34
     Leu Ser Ala Arg Lys Leu Leu Gln Asp Ile Met Ser Arg Gln Gln Gly Glu Ser
     CTG TCT GCT CGT AAA CTG CTG CAG GAC ATC ATG TCC CGT CAG CAG GGT GAA TCT
     GAC AGA CGA GCA TTT GAC GAC GTC CTG TAG TAC AGG GCA GTC GTC CCA CTT AGA
                                 Pst I              (Sal I)           PvuII
                                                                      (AvrII)

35  36  37  38  39* 40  41  42  43  44                ENTEROKINASE    CYS
     Asn Gln Glu Arg Gly Ala Arg Ala Arg Leu              Ala Met Leu Asp Asp Cys
     AAC CAG GAA CGT GGT GCT CGT GCT CGT CTG              GCT ATG CTC GAG GAC TGC
     TTG GTC CTT GCA CCA CGA GCA CGA GCA GAC              CGA TAC GAG CTC CTG ACG
                         (Sac I)
```

-hCAII
```
    Glu Phe Gly Gly Arg Gly Gly Gly Gly Val Asn Gly Pro Arg Gly Cys Ala Val Asp
    GAA TTT GGC GGC CGC GGT GGT GGT GGT GTT AAC GGT CCG CGT GGT TGC GCT GTC GAC
    CTT AAA CCG CCG GCG CCA CCA CCA CCA CAA TTG CCA GGC GCA ACG CGA CAG CTG
        ApoI    NotI                         HpaI                      SalI
                                                      THROMBIN      C/A
```

GLP1
```
CNBr7  8   9   10  11  12  13  14  15  16  17  18  19  20  21  22  23  24  25
    Met His Ala Glu Gly Thr Phe Thr Ser Asp Val Ser Ser Tyr Leu Glu Gly Gln Ala Ala
    ATG CAT GCT GAA GGT ACC TTC ACC TCC GAC GTT TCC TCC TAC CTG GAA GGT CAG GCT GCT
    TAC GTA CGA CTT CCA TGG AAG TGG AGG CTG CAA AGG ATG GAC CTT CCA GTC CGA CGA
        NsiI        KpnI
        SphI
```

```
26  27  28  29  30  31  32  33  34  35  36   C/A
Lys Glu Phe Ile Ala Trp Leu Val Lys Gly Arg Cys Ala Leu Glu Stop
AAA GAA TTC ATC GCT TGG CTG GTT AAA GGT CGT TGC GCT CTC GAG TAA GTC GAC
TTT CTT AAG TAG CGA ACC GAC CAA TTT CCA GCA ACG CGA GAG CTC ATT CAG CTG
    EcoRI                                        XhoI        SalI
```

FIG. 6A

-hCAII

| | | | | | | | | | | | | | | | | | | |
|---|---|---|---|---|---|---|---|---|---|---|---|---|---|---|---|---|---|---|
|Glu|Phe|Gly|Gly|Arg|Gly|Gly|Gly|Gly|Val|Asn|Gly|Pro|Arg|Gly|Cys|Ala|Val|Asp|
|GAA|TTT|GGC|GGC|CGC|GGT|GGT|GGT|GGT|GTT|AAC|GGT|CCG|CGT|GGT|TGC|GCT|GTC|GAC|
|CTT|AAA|CCG|CCG|GCG|CCA|CCA|CCA|CCA|CAA|TTG|CCA|GGC|GCA|CCA|ACG|CGA|CAG|CTG|

Sites: ApoI, NotI, HpaI, THROMBIN, C/A, SalI

GLP1

| CNBr | 7 | 8 | 9 | 10 | 11 | 12 | 13 | 14 | 15 | 16 | 17 | 18 | 19 | 20 | 21 | 22 | 23 | 24 | 25 |
|---|---|---|---|---|---|---|---|---|---|---|---|---|---|---|---|---|---|---|---|
|Met|His|Ala|Glu|Gly|Thr|Phe|Thr|Ser|Asp|Val|Ser|Ser|Tyr|Leu|Glu|Gly|Gln|Ala|Ala|
|ATG|CAT|GCT|GAA|GGT|ACC|TTC|ACC|TCC|GAC|GTT|TCC|TCC|TAC|CTG|GAA|GGT|CAG|GCT|GCT|
|TAC|GTA|CGA|CTT|CCA|TGG|AAG|TGG|AGG|CTG|CAA|AGG|AGG|ATG|GAC|CTT|CCA|GTC|CGA|CGA|

Sites: NsiI, SphI, KpnI

| 26 | 27 | 28 | 29 | 30 | 31 | 32 | 33 | 34 | 35 | 36 | C/A | | | | CNBr? | | | | |
|---|---|---|---|---|---|---|---|---|---|---|---|---|---|---|---|---|---|---|---|
|Lys|Glu|Phe|Ile|Ala|Trp|Leu|Val|Lys|Gly|Arg|Cys|Ala|Leu|Asp|Met|His|Ala|Gly|Gly|
|AAA|GAA|TTC|ATC|GCT|TGG|CTG|GTT|AAA|GGT|CGT|TGC|GCT|CTC|GAC|ATG|CAT|GCT|GGT|GGT|
|TTT|CTT|AAG|TAG|CGA|ACC|GAC|CAA|TTT|CCA|GCA|ACG|CGA|GAG|CTG|TAC|GTA|CGA|CCA|CCA|

Sites: EcoRI, NsiI, SphI, KpnI

GLP1

Positions 7, 8, 9, 10:
His Ala Glu Gly
CAT GCT GAA GGT
GTA CGA CTT CCA

FIG. 6B

```
     11   12  13   14   15   16   17   18   19   20   21   22   23   24   25   26   27   28   29   30
     Thr  Phe Thr  Ser  Asp  Val  Ser  Ser  Tyr  Leu  Glu  Gly  Gln  Ala  Ala  Lys  Glu  Phe  Ile  Ala
     ACC  TTC ACC  TCC  GAC  GTT  TCC  TCC  TAC  CTG  GAA  GGT  CAG  GCT  GCT  AAA  GAA  TTC  ATC  GCT
     TGG  AAG TGG  AGG  CTG  CAA  AGG  AGG  ATG  GAC  CTT  CCA  GTC  CGA  CGA  TTT  CTT  AAG  TAG  CGA
                                                                                        ‾‾‾‾‾‾‾‾
                                                                                          EcoRI

C/A
     31   32   33   34  35   36
     Trp  Leu  Val  Lys Gly  Arg  Cys  Ala  Leu  Glu  Stop
     TGG  CTG  GTT  AAA GGT  CGT  TGC  GCT  CTC  GAG  TAA  GTC  GAC
     ACC  GAC  CAA  TTT CCA  GCA  ACG  CGA  ACG  CTC  ATT  CAG  CTG
                                              ‾‾‾‾‾‾‾           ‾‾‾‾‾‾‾
                                                XhoI             (Sal I)
```

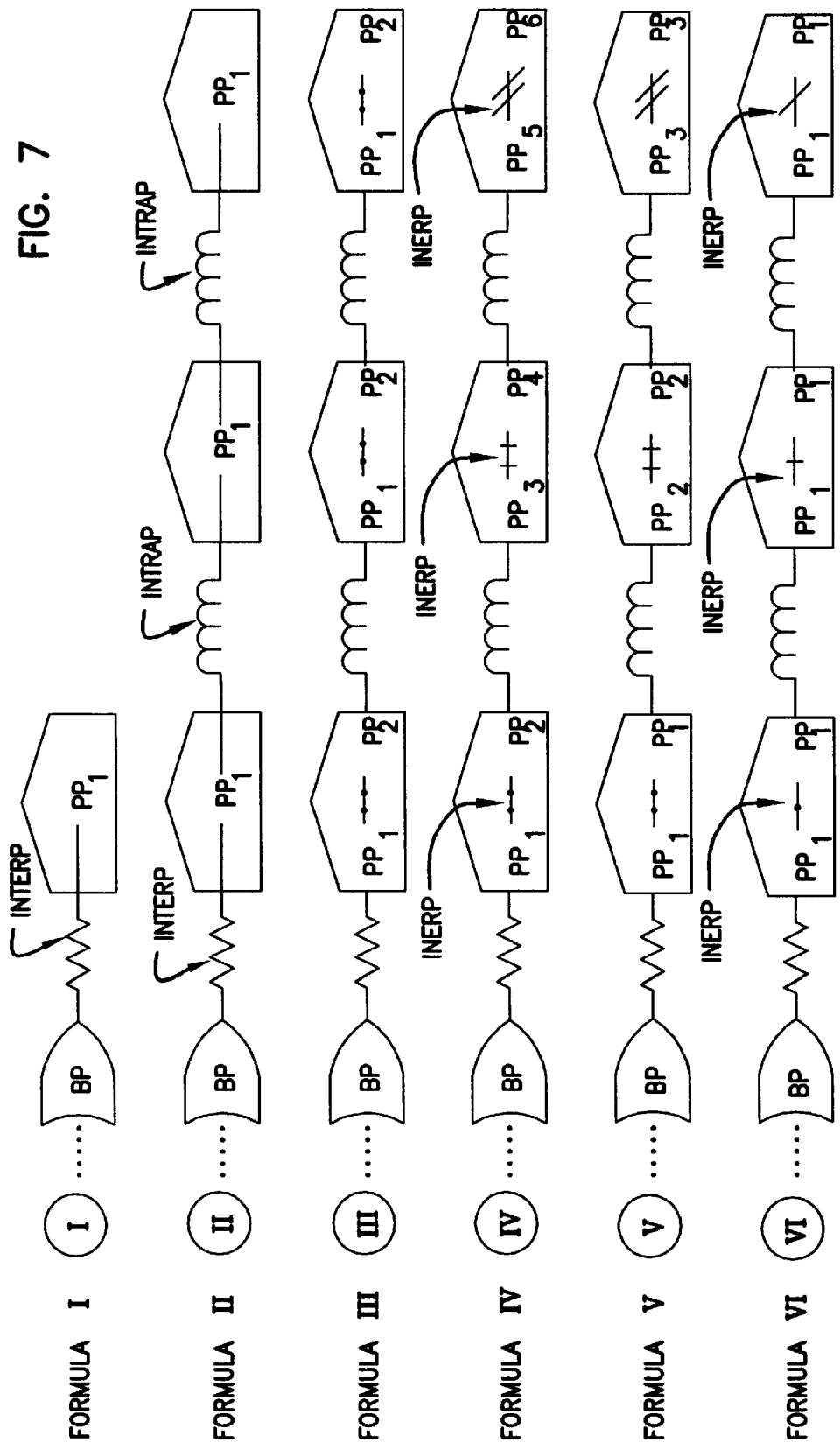

PRODUCTION OF C-TERMINAL AMIDATED PEPTIDES FROM RECOMBINANT PROTEIN CONSTRUCTS

This is a Continuation of application Ser. No. 08/350,528, filed Dec. 7, 1994 (now abandoned).

BACKGROUND OF THE INVENTION

In vitro DNA manipulation and the attendant transfer of genetic information have developed into a technology that allows the efficient expression of endogenous and foreign proteins in microbial hosts. Recombinant DNA techniques have made possible the selection, amplification and manipulation of expression of proteins and peptides. For example, changes in the sequence of the recombinantly produced proteins or peptides can be accomplished by altering the DNA sequence by techniques like site-directed or deletion mutagenesis.

Some modifications to a recombinantly produced protein or peptide, however, cannot be accomplished by altering the DNA sequence. For example, while the C-terminal α-carboxyl group in many naturally occurring protein and peptides often exists as an amide, this amide typically is not produced directly through expression. Rather, a precursor protein is produced by expression and the amide is biologically produced in vivo from the precursor protein.

Moreover, although expression of any foreign protein in any microbial host is theoretically possible, the stability of the protein produced often limits such practice and results in a low yield. In particular, small foreign proteins and oligopeptides cannot be overproduced in most cellular hosts. Expression of a small peptide in a host cell raises the possibility that the host will assimilate the peptide. For example, where size of the desired peptide is no more than about 60 to 80 amino acid units in length, degradation usually occurs rather than end product accumulation.

In response to this problem, small peptides have been expressed as part of fusion proteins which include a second larger peptide, such as a marker peptide (e.g., β-galactosidase or chloramphenicol acetyl transferase). While the use of a fusion protein may avoid assimilation, this approach may lead to other problems. Purification is often not very efficient or effective. Many of the marker peptides are such large molecular weight proteins that the desired protein constitutes only a small fraction of the fusion protein.

Another approach involves the expression of a recombinant construct which includes multiple copies of the desired peptide (a multicopy construct). The multicopy construct may or may not include a marker peptide or other leader sequence. Typically, the multicopy construct is designed so that the molecular weight is sufficient to prevent assimilation by the host cell.

The multicopy approach has typically been carried out with methionine residues positioned between the desired peptides. While such constructs can be selectively cleaved with cyanogen bromide, the use of multicopy construct with methionine cleavage sites is limited to the production of product peptides which lack a methionine residue (Met). In addition, cleavage of a multicopy construct at a methionine produces peptides with a C-terminal homoserine (Hse) lactone. This unnatural amino acid residue can be converted to the free acid or amide by ring opening. The amidated peptide, however, contains the unnatural amino acid residue, homoserine, as its C-terminal residue. Thus, known multicopy based methods which make use of methionine as a cleavage site do not permit the production of α-amidated forms of native peptide sequences.

Other reports of multicopy-based peptide production disclose the use of an acid sensitive cleavage site, -Asp-Pro-, or a tripeptide linker sequence which is cleaved by a specific pair of proteases (trypsin and α-chymotrypsin). Neither of these methods, however, permits the generation of the α-amidated form of peptides without placing some limitation on the amino acid sequence of the product peptide.

Accordingly, there is a continuing need for efficient flexible, inexpensive and convenient methods for the recombinant production of C-terminal amidated peptides. In particular, there is a need for methods which permit the production of a recombinant peptide in its α-amidated form without any limitations as to the amino acid sequence of the peptide. It is therefore an object of the present invention to provide an improved method for the production of a recombinantly produced C-terminal α-amidated peptide. A further object is to provide a simple and efficient method for modification of a recombinantly produced peptide which permits the exchange of an unnatural C-terminal homoserine residue with the amidated form of another amino acid. These and other objects are accomplished by the present invention.

SUMMARY OF THE INVENTION

The present invention provides a method for the production of C-terminal amidated recombinant peptides regardless of their sequence. The method allows the efficient production of peptides which cannot normally be obtained through recombinant technology. Typically, a recombinant protein construct having multiple copies of a target peptide is employed. The target peptide units are linked by intraconnecting peptides which permit the multicopy construct to be selectively reacted to produce product peptides having a C-terminal α-carboxamide. The recombinant protein construct may also include a adjunct peptide. The adjunct peptide generally is located near the N-terminus of the construct.

In one embodiment of the invention, the multicopy construct is cleaved to directly produce product peptides having a C-terminal α-carboxamide. In another embodiment, the multicopy construct is cleaved to precursor peptides which can be modified in a controlled manner to generate the desired C-terminal α-amidated product peptides.

Target peptides free of methionine residues may be produced using the present method. Target peptides of this type may be produced from a multicopy construct having intraconnecting peptides which include a methionine residue. Where the methionine residue is directly linked to the C-terminus of the target peptide, the multicopy construct may be cleaved with cyanogen bromide. The resulting fragments may be transpeptidated using a carboxypeptidase, e.g., a serine carboxypeptidase such as carboxypeptidase Y, to replace the C-terminal homoserine residue with an α-amidated amino acid. The fragments may be also transamidated with the carboxypeptidase to replace the C-terminal homoserine residue with a 2-nitrobenzylamine compound. This produces a fragment having a C-terminal (2-nitrobenzyl)amido group which may be photochemically decomposed to produce an α-amidated peptide fragment minus the homoserine residue.

The present method is particularly suitable for producing peptides from a recombinant protein construct including at least two copies of a target peptide free of unblocked cysteine residues. The target peptides are preferably linked by intraconnecting peptides which include a cysteine residue. If the cysteine residue is directly adjacent the C-terminus of the target peptide, the construct may be cleaved by an aminolysis reaction to a first α-amidated peptide. This is achieved by reacting the cysteine residue with an S-cyanylating agent to form an S-derivatized cysteine residue (activation) and reacting the S-derivatized cysteine residue with an amino compound (aminolysis). More preferably, the intraconnecting peptides include a second cleavage site which permits the N-terminal residues of the first α-amidated peptide to be cleaved to produce a desired α-amidated product peptide.

Another embodiment of the invention provides a recombinant protein construct which includes an amino acid sequence of the formula:

Yyy-(CS1)-TargP-(Cys)-Xxx wherein the Yyy- is a leader group, -(CS1)- is a cleavage site, the -TargP- is a target peptide and -Xxx is a tail group. The target peptide and the -(CS1)- cleavage site are free of unblocked cysteine residues.

C-terminal α-amidated peptides may also be produced by the present method from a multicopy construct containing copies of a target peptide which includes both a methionine residue and a cysteine residue. Furthermore, the C-terminal α-amidated peptide may be produced by simultaneously cleaving and transpeptidating with an endopeptidase.

BRIEF DESCRIPTION OF THE FIGURES

FIG. 1 depicts a portion of plasmid pBN1: PTH(1–34)C-$1_c$ (SEQ ID NO:1) (and corresponding amino acid sequence (SEQ ID NO:2)) coding for a fusion protein construct containing a single copy of PTH(1–34)(SEQ ID NO:56).

FIG. 2 depicts a portion of plasmid pBN1: PTH(1–34)C-$2_c$ (SEQ ID NO:3) (and corresponding amino acid sequence (SEQ ID NO:4)) coding for a fusion protein construct containing two copies of PTH(1–34)(SEQ ID NO:56).

FIG. 3 depicts a portion of plasmid pBN2: GRF(1–44)C-$1_c$ (SEQ ID NO:5) (and corresponding amino acid sequence (SEQ ID NO:6)) coding for a fusion protein construct containing a single copy of GRF(1–44) (SEQ ID NO:57).

FIG. 4 depicts a portion of plasmid pBN2: GRF(1–44)C-$2_c$ (SEQ ID NO:7) (and corresponding amino acid sequence (SEQ ID NO:8)) coding for a fusion protein construct including two copies of GRF(1–44) (SEQ ID NO:57).

FIG. 5 depicts a portion of plasmid pBN1: GLP(7–36)C-$1_c$ (SEQ ID NO:9) (and corresponding amino acid sequence (SEQ ID NO:10)) coding for a fusion protein construct including a single copy of GLP1(1–36) (SEQ ID NO:51).

FIG. 6 depicts a portion of plasmid pBN1: GLP(7–36)C-$2_c$ (SEQ ID NO:11) (and corresponding amino acid sequence (SEQ ID NO:12)) coding for a fusion protein construct including two copies of GLP1(1–36) (SEQ ID NO:51).

FIG. 7 depicts the various formulas for a portion of the fusion protein construct formed of multiple units of target peptides.

DETAILED DESCRIPTION OF THE INVENTION

The present method of producing a C-terminal α-amidated peptide typically includes cleaving a recombinant protein construct which includes an amino acid sequence of the formula:

Yyy-TargP'-(CS2)-[-(Ln1)$_n$-(CS1)$_m$-TargP-(CS2)- ]$_r$-Xxx where -CS1- and -CS2- are cleavage sites, -(Ln1)- is a linking peptide, -TargP'- and -TargP- are a target peptide, n and m are 0 or 1, and r is an integer from 1 to about 150. The Yyy- is a leader group and -Xxx is a tail group. The -CS2- cleavage site may be either an enzymatic or chemical cleavage site. In a preferred embodiment of the invention, the -CS2- cleavage site is either a methionine residue or an unblocked cysteine residue and the target peptide is free of at least one amino acid residue selected from the group consisting of a methionine residue and an unblocked cysteine residue.

The size of the recombinant protein construct will vary depending on the nature and number of copies of the target peptide. The recombinant protein construct is large enough to avoid degradation by the host cell (e.g., at least about 60 to 80 amino acid residues) and not so large that it can not be effectively expressed by the host cell. As a practical matter, the recombinant protein construct will have a molecular weight of up to about 500,000 although larger constructs are also within the scope of the present invention. The size of the recombinant protein construct is chosen such that it may be expressed by the host cell so as to avoid introducing errors in the protein sequence. This places practical limitations on the number of copies of the target peptide present in a given construct. The actual number will vary depending on the size and nature of a particular target peptide within the limitations set by the factors discussed above.

The linking peptide may have one of a number of forms. In the simplest form, the linking peptide functions as a spacer unit. In another form, the linking peptide may include a additional peptide segment (a second target peptide). A third form is a single unit composed of several (i.e., two or more) identical or different peptide segments tandemly interlinked together by innerconnecting peptides. Yet another form is composed of repeating multiple tandem units linked together by connecting peptides wherein each unit contains the same series of different individual target peptides joined together by innerconnecting peptides. The innerconnecting peptides may include a cleavage site which may be the same or different from cleavage sites present in the interconnecting peptides or intraconnecting peptides. The forms described above are merely examples which illustrate the variations and modifications which may be made in the linking peptide (see FIG. 7 for schematic depiction of protein constructs formed of multiple units of target peptides).

The target peptide may incorporate all or a portion of any natural or synthetic peptide desired as a product, e.g., any desired protein, oligopeptide or small molecular weight peptide. For the purposes of this application a peptide includes at least two amino acid residues linked by a peptide bond. Suitable embodiments of the target peptide include caltrin, calcitonin, insulin, tissue plasminogen activator, growth hormone, growth factors, growth hormone releasing factors, erythropoietin, interferons, interleukins, oxytocin, vasopressin, ACTH, collagen binding protein, glucagon like peptides, glucagon, parathyroid hormone, angiotensin, individual heavy and light antibody chains, individual chain fragments especially such as the isolated variable regions (VH or VL) as characterized by Lerner, Science, 246, 1275 et. seq. (Dec. 1989) and epitopal regions such as those characterized by E. Ward et al., Nature, 341, 544–546 (1986) wherein the antibodies, chains, fragments and regions have natural or immunogenetically developed antigenicity toward antigenic substances. Additional embodiments of the desired peptide include peptides having physiologic properties, such as sweetening peptides, mood altering peptides, nerve growth factors, regulatory proteins, functional hormones, enzymes, DNA polymerases, DNA modification enzymes, structural peptides, peptide analogs, neuropeptides, peptides exhibiting effects upon the cardiovascular, respiratory, excretory, lymphatic, immune, blood, reproductive, cell stimulatory and physiologic functional systems, leukemia inhibitor factors, antibiotic and bacteriostatic peptides (such as cecropins, attacins, apidaecins), insecticidal, herbicidal and fungicidal peptides as well as lysozymes.

The leader group (Yyy) includes at least one amino acid residue. The leader group may also include a peptide, e.g., an adjunct peptide, or a cleavage site. In a preferred embodiment of the invention, the leader group includes a ligand binding protein, a highly charged peptide, an antigenic peptide, a polyhistidine-containing peptide, a hydrophobic peptide, or a DNA binding peptide. In another preferred embodiment of the invention, the leader group includes a cleavage site connected to the N-terminus of the -TargP'- target peptide.

The tail group (Xxx) may be a hydrogen or may include an amino acid residue or a peptide such as the adjunct peptide. Typically, the tail group includes a single amino acid or a short sequence of amino acids (e.g., up to about 10 amino acid residues). This facilitates the insertion of restriction enzyme sites into a recombinant DNA construct coding for the recombinant protein construct.

The recombinant protein construct may also include a adjunct peptide. The adjunct peptide may be included as part or all of either the leader group (Yyy) or the tail group (Xxx). Typically, the adjunct peptide is located near the N-terminus of the construct. The adjunct peptide may aid in preventing the assimilation of the construct by the host cell during expression and may also facilitate the isolation and/or purification of the construct. The adjunct peptide may include a ligand binding protein, a highly charged peptide, an antigenic peptide, a polyhistidine-containing peptide, a hydrophobic peptide, or a DNA binding peptide. All of these types of adjunct peptides allow the recombinant protein construct to be selectively removed from other cellular components. In a preferred version of the invention, the adjunct peptide includes a carbonic anhydrase (e.g., human carbonic anhydrase) or a modified functional version thereof. Suitable carbonic anhydrase adjunct peptides and their modified functional versions are described in U.S. Pat. No. 5,595,987 the disclosure of which is herein incorporated by reference.

The fusion protein construct may include a chemical cleavage site or an enzymatic cleavage site. The cleavage site or sites which may be incorporated into the fusion protein construct will depend upon the identity of the target peptide(s) present. The cleavage site and target peptide are typically selected so that target peptide does not contain an amino acid sequence corresponding to the cleavage site. Secondary considerations will also influence the choice of a particular cleavage site. In some instances, the cleavage sites may be designed so as to avoid the use of a enzymatic cleavage reaction. This may be accomplished by employing a chemical cleavage site, such as a site which may by cleaved after treament with an S-cyanylating agent (e.g, 2-nitro-5-thiocyanatobenzoate) or by treatment with an acid having a $pK_a$ of no more than about 3.0. In other instances, it may be desireable to employ a cleavage site which permits a modification of the target peptide to introduce a specific functional group, e.g., a C-terminal α-carboxamide group. It may also be desirable to incorporate an endopeptidase cleavage site in the recombinant protein construct, e.g., to facilitate the removal of an N-terminal tail sequence from fragments generated from the recombinant protein construct. Examples of suitable endopeptidases include enterokinase, Factor Xa, ubiquitin cleaving enzyme, thrombin, trypsin, renin, subtilisin, chymotrypsin, clostripain, papain, ficin, and S. aureus V8.

Chemical and enzymatic cleavage sites and the corresponding agents used to effect cleavage of a peptide bond close to one of these sites are described in detail in copending U.S. Pat. Nos. 5,595,987 and 5,512,459 the disclosure of which is herein incorporated by reference. Examples of peptide sequences (and DNA gene sequences coding therefor) suitable for use as cleavage sites in the present invention and their corresponding cleavage enzymes or chemical cleavage conditions are shown in Table 1 below. The gene sequence indicated is one possibility coding for the corresponding peptide sequence. Other DNA sequences may be constructed to code for the same peptide sequence.

TABLE 1

|  | Peptide Sequence | DNA Sequence |
|---|---|---|
| Enzymes for Cleavage | | |
| Enterokinase | (Asp)$_4$Lys (SEQ ID NO: 14) | GACGACGACGATAAA (SEQ ID NO: 13) |
| Factor Xa | IleGluGlyArg (SEQ ID NO: 16) | ATTGAAGGAAGA (SEQ ID NO: 15) |
| Thrombin | GlyProArg or GlyAlaArg | GGACCAAGA or GGAGCGAGA |
| Ubiquitin Cleaving Enzyme | ArgGlyGly | AGAGGAGGA |
| Renin | HisProPheHisLeu-LeuValTyr (SEQ ID NO: 18) | CATCCTTTTCATC-TGCTGGTTTAT (SEQ ID NO: 17) |
| Trypsin | Lys or Arg | AAA OR CGT |
| Chymotrypsin | Phe or Tyr or Trp | TTT or TAT or TGG |
| Clostripain | Arg | CGT |
| S. aureus V8 | Glu | GAA |
| Chemical Cleavage | | |
| (at pH3) | AspGly or AspPro | GATGGA or GATCCA |
| (Hydroxylamine) | AsnGly | AATCCA |
| (CNBr) | Methionine | ATG |

TABLE 1-continued

| | Peptide Sequence | DNA Sequence |
|---|---|---|
| BNPS-skatole | Trp | TGG |
| 2-Nitro-5-thiocyanatobenzoate | Cys | TGT |

The present method is particularly useful for producing amidated forms of peptides which lack an unblocked cysteine residue, i.e., lack a cysteine residue having a free sulfhydryl group (-SH). Examples of blocked cysteine residues include cystine residues where the sulfur atom is part of a disulfide group (-SS-) and derivatives of cysteine where the hydrogen of the sulfhydryl group has been replaced by a protecting group, e.g., an S-benzylated cysteine residue.

Examples of peptides which lack an unblocked cysteine residue include peptides free of unblocked cysteine residues having a molecular weight of 300 to about 200,000, preferably 400 to 10,000. Such peptides typically include 3 to 100 amino acids residues, preferably 3 to 70 residues. Examples of such peptides include adrenocorticotropic hormone (ACTH), parathyroid hormone (PTH), enkephalins, endorphins, various opioid peptides, β-melanocyte stimulating hormone, glucose-dependent insulinotropic polypeptide (GIP), glucagon, glucagon-like peptides (GLP-I and II), growth hormone-releasing factor (GRF), motilin, thymopoietins, thymosins, ubiquitine, serum thymic factor, thymic humoral factor, various quinines, neurotensin, tuftsin and fragments of these peptides.

The present invention may also be used to produce the α-amidated form of peptides having an -S-S- linkage in their structure. These are also included in the desired peptide. Examples of peptides having amide at their C-terminus and/or an -S-S- linkage include gastrin, calcitonin, calcitonin gene associated peptide, cholecystokinin-pancreozymin (CCK-PZ), eledoisin, epithelial growth factor (EGF), tumor growth factor (TGF-α), pancreastatin, insulin, insulin-like growth factors, luteinizing hormone-releasing hormone (LH-RH), mellitin, oxytocin, vasopressins, pancreatic polypeptide, trypsin inhibitor, relaxin, secretin, somatostatins, somatomedins, substance P, neurotensin, caerulein, thyrotropin-releasing hormone (TRH), vasoactive intestinal polypeptide (VIP), pituitary adenyl cyclase-activating polypeptides (PACAPs), gastnin-releasing peptide (GRP), endotherins, corticotropin-releasing factor (CRF), PTH-related protein, gallanin, peptide YY, neuropeptide Y, pancreastatin, atrial natriuretic peptides and fragments of these peptides.

The target peptides free of unblocked cysteine residues are preferably linked by intraconnecting peptides which include a cysteine residue. If the cysteine residue is directly adjacent the C-terminus of the target peptide, the construct may be cleaved by an aminolysis reaction to provide a first α-amidated peptide. This is achieved by reacting the cysteine residue with an S-cyanylating agent to form an S-derivatized cysteine residue (activation) and reacting the S-derivatized cysteine residue with an amino compound (aminolysis). More preferably, the intraconnecting peptides include a second cleavage site which permits the N-terminal residues of the first α-amidated peptide to be cleaved to produce a desired α-amidated product peptide.

The S-cyanylating agent may include a thiocyanato substituted aromatic compound or a 1-cyano-4-(dialkylamino) pyridinium salt. Suitable examples of the thiocyanato substituted aromatic compound include 4-nitro-thiocyanatobenzene compounds such as 2-nitro-5-thiocyanatobenzoic acid and its salts. Suitable examples of the 1-cyano-4-(dialkylamino)pyridinium salt include 1-cyano-4-(dimethylamino)pyridinium tetrafluoroborate (DMAP-CN), 1-cyano-4-(N-methyl,N-benzylamino) pyridinium tetrafluoro-borate and 1-cyano-4-(pyrrolidino)-pyridinium tetrafluoroborate.

A wide variety of amino compounds may be employed in the aminolysis reaction for cleaving the N-terminal peptide linkage of the derivatized cysteine residue to produce an α-amidated peptide. The amino compound may be ammonia or may be a mono- or disubstituted amine (a "substituted amino compound"). Preferably the amino compound is ammonia or a monosubstituted amine.

The substituent(s) on the substituted amine may be (i) $C_{1-20}$ alkyl, $C_{3-8}$ cycloalkyl, or aryl-$C_{1-3}$ alkyl, which may have no substituent or one to three substituent(s) on their carbon atoms, (ii) amino or alkyl substituted amino, or (iii) hydroxyl or $C_{1-6}$ alkoxy group. Examples of $C_{1-20}$ alkyl substituents includes methyl, ethyl, isopropyl, sec-butyl, neopentyl, octyl, dodecanyl and hexadecanyl. Suitable examples of $C_{3-8}$ cycloalkyl substituents include cyclopentyl, cyclohexyl and methylcyclohexyl. Examples of aryl-$C_{1-3}$ alkyl substituents include benzyl, phenethyl, 3-phenylpropyl and (2-naphthyl)methyl. Examples of $C_{1-6}$ alkoxy group substituents include methoxy, ethoxy, isopropoxy, and hexyloxy.

The substituted amino compound may also be an amino acid or a peptide, e.g., a peptide having from two to about 10 amino acids residues. The α-carboxy group of the amino acid may be in the carboxy form or may be present as a carboxamide. The C-terminal amino acid residue of the peptide may be also be present in the α-carboxy form or as an α-carboxamide. Examples of the amino acid include L- or D-isomer of natural amino acids, such as glycine, alanine or arginine, as well as synthetic amino acids.

The amount of S-cyanylation reagent is about 2 to 50 times, preferably about 5 to 10 times the total amount of all thiol groups. The cyanylation reaction is typically carried out at a temperature in the range from about 0 to 80° C., preferably between about 0 and 50° C. Any buffer can be used as a solvent, as long as it does not react with the cyanylating reagent. Examples of such buffers include Tris-HCl buffer, Tris-acetate buffer, phosphate buffer and borate buffer. An organic solvent may be present, as long as it does not react with the cyanylating reagent.

The cyanylation reaction is normally carried out at a pH of between 1 and 12. Particularly when using NTCB, a pH range of from 7 to 10 is preferred. When using DMAP-CN, a pH range of from 2 to 7 is preferred, to avoid S-S exchange reaction. The reaction mixture may also contain a denaturant such as guanidine hydrochloride or urea. Under the conditions described above, cyanylation typically is complete within about 10–60 minutes, preferably about 15–30 minutes, although longer reaction times may also be employed.

The derivatized cysteine produced by the S-cyanylation reaction is allowed to react with the amino compound under basic conditions. The pH of the solution is typically determined by the base strength of the amino compound. The amino compound is usually present in the aminolysis reaction mixture at a concentration of about 0.01–15M, and preferably about 0.1–3M.

The derivatized cysteine produced by the S-cyanylation reaction may also be allowed to react with hydroxide (e.g., by adding sodium hydroxide) to produce an intermediate peptide having a C-terminal α-carboxylic acid group. The intermediate peptide may be transpeptidated with an amidated amino acid in the presence of an exopeptidase to produce a C-terminal amidated peptide. Alternatively, where the intermediate peptide includes a C-terminal glycine residue, the terminal glycine residue may be decomposed in the presence of a glycine monooxygenase to produce a C-terminal amidated peptide. The intermediate peptide may also be transamidated with a 2-nitrobenzylamine compound in the presence of a carboxypeptidase to replace the C-terminal intermediate peptide residue with a C-terminal (2-nitrobenzyl)amido group. The (2-nitrobenzyl)amido group may then be photochemically decomposed to produce a C-terminal amidated peptide.

The present invention provides a method of producing an amidated peptide from a recombinant construct which includes a target peptide free of methionine residues. Suitable examples of target peptides lacking a methionine residue include GLP1(1–36) (SEQ ID NO:57), GLP1(7–35) (SEQ ID NO:52), GLP1(7–36) (SEQ ID NO:53), and calcitonin. Preferably, the construct includes two or more copies of the target peptide.

The recombinant protein construct may include multiple copies of a methionine-free target peptide flanked on both ends by a methionine. Constructs of this type may be cleaved into precursor peptides by treatment with cyanogen bromide (CNBr). The precursor peptides are capable of being modified in a controlled manner to generate the desired C-terminal α-amidated product peptides. For example, a recombinant protein construct having a methionine residue as the -(CS2)- cleavage site may be treated with cyanogen bromide to produce a precursor peptide having a C-terminal homoserine residue. The precursor peptide with the homoserine residue in its acid form may then be transamidated, e.g., by treatment with a carboxypeptidase in the presence of an α-amidated amino acid to produce an amidated product peptide.

In a preferred version of the invention, the target peptides, which lack a methionine residue, are linked solely by a methionine (i.e., n and m are 0). Treatment of the recombinant protein construct with cyanogen bromide provides a fragment having the formula TargP-Hse. If the TargP-Hse fragment is present as its α-carboxylic acid form, the fragment may be transamidated with a carboxypeptidase, thereby replacing the terminal homoserine residue. The transamidation permits the homoserine residue to be replaced with either an α-amidated amino acid or a 2-nitrobenzylamine compound.

Transamidation of the TargP-Hse fragments in the presence of a carboxypeptidase may be employed to replace the C-terminal homoserine residue with a 2-nitrobenzylamine compound. Examples of suitable 2-nitrobenzylamine compounds include 2-nitrobenzylamine, (2-nitrophenyl) glycinamide (ONPGA) and 1-(2-nitrophenyl)-ethylamine. The transamidation reaction produces fragments C-terminated in an (2-nitrobenzyl)amido group, e.g., TargP-NH-(2-nitrobenzyl). The (2-nitrobenzyl)amido fragments may be decomposed by irradiation with long wavelength UV light (e.g., λ no longer than about 320 nm) resulting in the replacement of the (2-nitrobenzyl)amido group with an NH$_2$ group. The transamidation and decomposition procedures are disclosed in Henriksen et al., *J.Am.Chem.Soc.*, 114, 1876 (1992), the disclosure of which is incorporated herein by reference.

Alternatively, the TargP-Hse fragments may be transpeptidated with an α-amidated amino acid in the presence of a carboxypeptidase such as carboxypeptidase Y. For example, the peptide fragment GLP1(1–35)-Hse (SEQ ID NO:54), may be subjected to transpeptidation with Arg—NH$_2$ in the presence of a suitable carboxypeptidase to produce GLP1 (1–36)-NH$_2$ (SEQ ID NO:51). One example of such a peptidase is described in U.S. application Ser. No. 08/144,704, the disclosure of which is herein incorporated by reference.

In another embodiment of the invention, the target peptide is free of methionine and unblocked cysteine residues. Target peptides of this type may be produced using a recombinant protein construct of the formula:

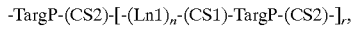

where the -(CS1)- cleavage site is a methionine residue, and the -(CS2)- cleavage site is a cysteine residue ("multicopy construct MC"), i.e., the variable polypeptides are connected by a -Cys-(Ln1)$_n$-Met- linking peptide. This recombinant protein construct may be cleaved by reacting the methionine residue with cyanogen bromide to produce fragments having a C-terminal homoserine residue. The peptide fragments may be reacted with an S-cyanylating agent to derivatize the cysteine residue. When the S-derivatized cysteine residue is treated with an amino compound, the remains of the linking peptide are cleaved at the N-terminal peptide bond of the derivatized cysteine residue to furnish an α-amidated peptide. Where the amino compound is a substituted amine (e.g., NH$_2$R where R is alkyl, alkoxy, —OH or —NH$_2$), the aminolysis reaction provides the corresponding substituted carboxamide, hydroxamic acid derivative or hydrazide.

Alternatively, the multicopy construct may be initially treated with the S-cyanylating agent. Cleavage of resulting cysteine-derivatized construct with an amino compound creates peptide fragments having a C-terminal α-amidated residue and the N-terminal tail sequence ITC-(Ln1)$_n$-Met- (where ITC represents the (iminothiazolinyl) carbonyl residue generated from the reaction of the derivatized cysteine). The fragments may be cleaved at the N-terminal peptide bond of the methionine residue to remove the N-terminal tail sequence and the furnish desired C-terminal α-amidated peptide.

In another version of this embodiment, after treating the multicopy construct with the S-cyanylating agent, the resulting cysteine-derivatized construct may be treated with CNBr to produce peptide fragments having a C-terminal tail sequence -drCys-(Ln1)$_n$-Hse- (where -drCys- represents a derivatized cysteine residue generated from the cyanylation reaction and -Hse- represents a homoserine residue). The fragments may be reacted with the amino compound to cleave the fragments at the N-terminal peptide bond of the -drCys- residue to remove the C-terminal tail sequence and the furnish an α-amidated peptide.

A suitable example of a recombinant protein construct having a target peptide is free of methionine and unblocked cysteine residues is a recombinant protein construct which includes tandemly linked multiple copies of the sequence -Ala-Met-GLP1(7–36) -Cys- (SEQ ID NO:55). This recombinant protein construct may be treated in sequence with CNBr, an S-cyanylating agent (e.g., NTCB or DMAP-CN) and an amino compound (HNRR') to produce the amidated peptide GLP1(7–36)-NRR' (SEQ ID NO:53).

Another embodiment of the invention provides recombinant protein construct which includes an amino acid sequence of the formula:

-Xxx-(CS1)-TargP-(Cys)- wherein the -Xxx- is an amino acid residue, the -(CS1)- is a cleavage site and the -TargP- is a target peptide. The target peptide and the -(CS1)- cleavage site are free of unblocked cysteine residues. The target peptide is also free of amino acid sequences corresponding to the -(CS1)- cleavage site. If the -(CS1)- cleavage site is a chemical cleavage site, such as Met, Asn-Gly, Asp-Gly, or Asp-Pro, the target peptide can be cut out of the recombinant protein construct without the use of an enzymatic step.

Amidated peptides may also be produced from a target peptide which may include both a methionine residue and a cysteine residue. Target peptides of this type are incorporated into a multicopy construct which includes an endopeptidase cleavage site. The endopeptidase cleavage site is preferably designed so that the construct may be simultaneously cleaved and transpeptidated with the endopeptidase to produce fragments having a C-terminal α-amidated amino acid residue. The transpeptidation reaction is carried out in the presence of an amino acid or peptide having a C-terminal α-carboxamide using an endopeptidase such as trypsin or thrombin. This method is described in detail in U.S. Pat. No. 5,595,987 the disclosure of which is herein incorporated by reference.

Methods for expression of single- and multicopy fusion recombinant polypeptide, e.g., a polypeptide expressed with a leader sequence, such as an affinity moiety attached to it, are known in the art and described in *Protein Purification: From Mechanisms to Large-Scale Processes*, Michael Ladisch, editor; American Chemical Society, publisher (1990), the disclosure of which is incorporated herein by reference. Methods for expression of multicopy protein constructs lacking a leader sequence are also known in the art (see, e.g., Kirshner et al., *J. Biotechnology*, 12: 247–260 (1989), and Shen, *Proc.Natl.Acad.Sci., USA*, 81, 4627 (1984), the disclosure of which is incorporated herein by reference).

The invention will be further described by reference to the following detailed examples.

EXAMPLE 1

Description of the Host Cells

The bacterial host for expression, *E. coli* BL21 F⁻ ompT r⁻$_B$ m⁻$_B$ (DE3) was obtained from Novagen, Inc., Madison, Wis. These *E. coli* cells give high levels of expression of genes cloned into expression vectors containing the bacteriophage T7 promoter. Bacteriophage (DE3) which contains the T7 RNA polymerase gene has been integrated into the chromosomal DNA of the BL21 (DE3) cells. The T7 RNA polymerase gene is controlled by the lacUV5 promoter and the laci gene.

EXAMPLE 2

Expression Plasmids Containing hCAII
Construction of pBN1

An expression vector, pET31F1mhCAII containing the hCAII gene was obtained from Dr. P. J. Laipis at the University of Florida. The pET31F1mhCAII was prepared as described by Tanhauser et al., *Gene*, 117, 113 (1992). Plasmid pET31F1mhCAII contains the coding region for hCAII (human carbonic anhydrase II) downstream of a bacteriophage T7 promoter in a pUC-derived plasmid backbone. Two synthetic oligonucleotides, 5'-A GCT TTC GTT GAC GAC GAC GAT ATC TT-3' (SEQ ID NO:19) and its complementary sequence 5'-AGC TAA GAT ATC GTC GTC GTC AAC GAA-3' (SEQ ID NO:20), were cloned into pET31F1mhCA2 which had been digested with Hind III. This plasmid was designated pA1 (see Table 2).

Plasmid pA1 was digested with the restriction endonucleases Ssp I and BspE I and the resulting ends were made blunt by treatment with T4 DNA polymerase. The DNA fragment from the pA1 digest containing the T7-hCAII-cassette was subcloned into the Sca I restriction site of pBR322 (New England Biolabs) thus conferring tetracycline resistance, but not ampicillin resistance. The resulting plasmid was designated pBN1.
Construction of pBN3

The pA1 plasmid was opened at the Hind III site and the EcoR V site and the synthetic oligonucleotide, 5'-A GCT GAA TTC AAC GTT CTC GAG GAT-3' (SEQ ID NO:21) and its complementary sequence 5'-ATC CTC GAG AAC GTT GAA TTC-3' (SEQ ID NO:22), were cloned into the vector. The insertion of these oligonucleotides provides a T7-hCAII-cassette containing unique EcoR I and Xho I restriction sites at the carboxyl terminal of hCAII. The resulting plasmid was designated pA3.

The pBN1 vector was digested with EcoR I and the single stranded overhangs were filled in with Polymerase I Large (Klenow) Fragment. The linear plasmid with newly formed blunt ends was religated, thus destroying the EcoR I site. The resulting plasmid was designated pBN3.

Plasmid pA3 was digested with the restriction endonucleases, Xba I and BspE I. The DNA fragment from the pA3 digest containing the T7-hCAII-cassinto was subcloned into the pBN1 vector which had been digested with Xba I and BspE I. The resulting vector was designated plasmid pBN4.

EXAMPLE 3

Expression Plasmid without hCAII

All the nucleotides coding for the hCAII gene were removed from the expression vector pBN1 by the following procedure. Two synthetic DNA strand were synthesized:

Oligo A: 5' AAT CTA GAA ATA ATT TTG TTT AAC TTT AAG AAG G (SEQ ID NO:23)

Oligo B: 5' TAG AAT TCC ATG GTA TAT CTC CTT CTT AAA (SEQ ID NO:24)

Oligonucleotides A and B were used in a PCR amplification of the primer-dimer. The PCR product was purified and digested with the restriction endonucleases EcoR I and Xba I. The resulting fragment was ligated into the vector pBN4, which had previously been digested with EcoR I and Xba I. The resulting vector, designated pBN5, contains unique sites for the restriction endonucleases Nco I and Xho I between the T7 promoter and the T7 terminator. Plasmid pBN5 may be used to form vectors coding for multicopy constructs having at least about 2 copies of a target peptide. The resulting plasmids may be used to transform host cells such as *E. coli* and express the multicopy constructs as part of inclusion bodies.

EXAMPLE 4

General Procedure for Preparation of Transformed Cell Lines

Competent *E. coli* cells were purchased from Novagen containing the DE3 bacteriophage. The *E. coli* BL21 (DE3) cells were transformed with the desired plasmid according to Sambrook et al., *Molecular Cloning, A Laboratory Manual*, Cold Spring Harbor Laboratory, N.Y. (1989). Ampicillin or tetracycline resistant clones (those containing the recombinant plasmid) were selected and subcultured for subsequent screening.

Selection Procedure

DNA was isolated from subcultured cells by conventional methods (Promega-Wizard Mini Prep Kit). The purified DNA was digested with specific restriction endonucleases to select clones containing the correct plasmids. Purified DNA from representative screened clones was subjected to DNA sequencing to confirm the presence of the gene for the fusion protein construct.

Isolation and Preservation of Cell Lines

E. coli cells containing the expression plasmid for the fusion protein were plated on LBT agar and incubated for 12 hours at 37° C. Using sterile conditions, several single cell isolates were transferred to culture flasks containing LBT broth supplemented with glucose at 1 mg/ml media and incubated at 37° C. with shaking for 12 to 16 hours.

To each of the culture flasks were added 50 ml of sterile glycerol containing 750 μg tetracycline. The contents of the flasks were thoroughly mixed then 1.0 ml aliquots are transferred to 2 ml cryovials under sterile conditions. The cryovials were cooled to −20° C. for 30 minutes, then transferred to a liquid nitrogen dewar and maintained at −176° C. The frozen vials of culture were used to prepare the inoculum.

EXAMPLE 5

General Procedure for Fermentation and Isolation of Inclusion Bodies

Preparation of the Inoculum

L-broth was sterilized in the autoclave at 121° C. for 20 minutes on the liquid cycle setting. The glucose and tetracycline stocks were filter sterilized by passage of the solution through a 0.22 μm filter. Two 250 ml shake flasks were each charged with the following solutions:

50 ml L-broth (1.0% tryptone, 1.0% NaCl, 0.5% yeast extract)

1.0 ml glucose stock (50 mg/ml)

150 μl tetracycline stock (5.0 mg/ml)

100 μl thawed inoculum of E. coli cells transformed with a vector coding for the desired hCA-fusion construct The shake flasks were placed in an incubator shaker at 37° C., 200–220 rpm for 10–14 hours. The optical density (O.D.) of the cells in the resulting solutions was then measured at 540 nm. A 1:25 dilution was usually necessary to obtain a proper reading. One of the two shake flasks was then chosen for inoculating the next set of shake flasks. Three 500 ml shake flasks were each charged with the following sterilized solutions:

200 ml L-broth (1.0% tryptone, 1.0% NaCl, 0.5% yeast extract);

4.0 ml glucose stock (50 mg/ml);

600 μl tetracycline stock (5.0 mg/ml);

1.0 ml inoculum from one of the first two shake flasks.

The three shake flasks were placed in an incubator shaker under the conditions described above and the cells were allowed to grow for 8–10 hours. The optical density of the resulting solutions was then measured at 540 nm (typically at a 1:25 dilution). All three shake flasks were then used to inoculate the fermentor.

Fermentation

Fermentation media was added to the fermentor and the volume was adjusted to 45.0 L with distilled $H_2O$. The media contained the following: 1200.0 g Casamino acids; 300.0 g Yeast extract; 30.0 g NaCl; and 0.10 ml Antifoam. The fermentor was sterilized at 121° C. for 25 minutes. The fermentor was cooled to 37° C. Before inoculation, the following solutions were added to the fermentor:

glucose (480.0 g in 800.0 ml $H_2O$)

magnesium (120.0 g $MgSO_4.H_2O$ in 250.0 ml $H_2O$)

phosphates (120.0 g $K_2HPO_4$ & 465.0 g $KH_2PO4$ in 3.0 l $H_2O$)

tetracycline (0.90 g tetracycline.HCl in 30.0 ml 95% EtOH & 20.0 ml $H_2O$)

mineral mix (Dissolved in 490.0 ml $H_2O$ & 10.0 ml concentrated HCl):

3.6 g $FeSO_4.7H_2O$ 3.6 g $CaCl_2.2H_2O$ 0.90 g $MnSO_4$ 0.90 g $AlCl_3.6H_2O$ 0.09 g $CuCl_2.2H_2O$ 0.18 g Molybdic Acid 0.36 g $CoCl_2.6H_2O$ All of the above solutions were sterilized for 20 minutes in the liquid cycle in an autoclave except for the tetracycline and mineral mix solutions. These were sterilized by passage through a 0.22 μm filter. At this point, the pH typically had dropped to approximately 6.5. If this had occurred, base (14.8 N ammonium hydroxide) was added to adjust the pH to 6.8. After the pH reached 6.8, 600.0 ml inoculum was added to the fermentor. The following parameters were monitored at time zero and throughout the fermentation: Glucose concentration (maintained at about 2–5 g/l); Optical Density; pH (6.8 is optimal); Dissolved Oxygen (40% is optimal); and Agitation. The temperature was maintained at 37° C. throughout the fermentation. Air intake was 40 l/min at the beginning of the fermentation. The initial dissolved oxygen concentration was 90% but quickly dropped to 40%. It was maintained at this level via increased agitation and oxygen supplementation throughout the fermentation. When oxygen supplementation was started, the air influx was reduced to 20 l/min. The initial glucose concentration was approximately 9 g/l but dropped to 5 g/l after about six hours. Once the glucose concentration dropped to this level, a glucose feed (70% w/v glucose) was used to maintain the glucose concentration at 5 g/l.

When the fermentation had proceeded to the point where an O.D. of 15–20 was measured, the media feed was started. The media feed consisted of 1200.0 g casamino acids and 300.0 g yeast extract dissolved in 5.0 l distilled $H_2O$ and autoclaved for 20 minutes on liquid cycle. The media feed was added to the fermentor over 1.0–1.5 hours. When fermentation had produced an O.D. of 30.0, the fermentation was induced by adding the following solutions to the fermentor: isopropylthiogalactoside (IPTG; 28.8 g in 200 ml distilled $H_2O$); $ZnCl_2$ (0.818 g in 50 ml distilled $H_2O$ with one drop of 6N HCl). The IPTG solution was filter sterilized through 0.22 μm filter. The $ZnCl_2$ solution was sterilized for 20 minutes, liquid cycle in the autoclave. After the addition, the concentration of IPTG in fermentor was 2.0 mM and the concentration of $ZnCl_2$ was 100 μM. A feed of a mixture of amino acids was then started at this point. The amino acid feed consisted of 225.0 g L-serine; 75.0 g L-tyrosine; 74.0 g L-tryptophan; 75.0 g L-phenylalanine; 75.0 g L-proline; and 75.0 g L-histidine; and was dissolved in a mixture of 1.5 l $H_2O$ and 500 ml concentrated HCl. The amino acid feed was sterile filtered through a 0.22 μm filter prior to addition to the fermentation. Induction was allowed to continue for 2.0 hours at which point the fermentation broth was transferred to a harvest tank and chilled to approximately 5–10° C. The fermentation typically yielded between 6.5 to 9.5 kg of wet cell paste (dry cell weight of about 1.0–1.5 kg).

Cell Harvest

The cell suspension from the fermentor as described above was concentrated over a tangential crossflow membrane to a volume of 10 l. The concentrated cell suspension was diafiltered and washed with 30 l of a cold wash buffer containing 50 mM Tris-SO4 pH 7.8, 1.0 mM EDTA, and 0.10 mM phenylmethylsulfonyl fluoride (PMSF). The cell suspension was then concentrated to 8 l. At this point, the concentrated cell suspension (cell paste) may be bagged and frozen for later processing or transferred to homogenizer holding tanks for cell lysis.

Cell Lysis

The cell paste obtained from the 60 l fermentor was diluted to 32 l in cold wash buffer (see above) and the resulting cell suspension was chilled to 5–10° C. The chilled cell suspension was homogenized at 12,000 psi with a Galin high pressure homogenizer. The homogenized cell paste was passed through a heat exchanger to chill the lysate to 10° C. and passed through the homogenizer a second time.

1100 base pair DNA fragment from pA1: PTH(1–34) containing the T7 expression cassette into the digested pBN1. The resulting plasmid was designated pBN1: PTH(1–34).

EXAMPLE 7

Expression Plasmid for PTH Single Copy with a Cyanylation Site

The following two DNA oligonucleotides are synthesized:

```
Oligo C: 5' TC AAA GCT TCT  GCC ATG GGC GGC CGC GTC GAC (SEQ ID NO: 33)
            CGT GGT CCG CGT TCT GTT TCT GAA ATC CAG Oligo D: 5' CTC GAT ATC TTA CTC GAG AGC GCA GAA GTT GTG (SEQ ID NO: 34)
            AAC GTC C
```

EXAMPLE 6

Expression Plasmid for PTH Single Copy

The preparation of the DNA segment coding for a single copy PTH(1–34) (SEQ ID NO:56) fusion protein was carried out by preparing an expression vector coding for a PTH-construct which included a DNA segment coding for the hCAII, an interlinking peptide, and PTH(1–34) (SEQ ID NO:56). The following oligonucleotides were obtained from Operon Technologies Inc, 1000 Atlantic Ave. Alameda CA 94501.

Oligonucleotide C includes Hind III, Nco I, Not I and Sal I sites positioned in front of a thrombin-cleavable linking peptide. Oligonucleotide D inserts a cysteine immediately after the PTH(1–34) (SEQ ID NO:56)followed by a a Xho I site, a stop codon and the EcoR V site.

The plasmid pBN1: PTH(1–34) is used as a template and the Oligonucleotides C and D are used as primers for the PCR amplification of the single copy gene.

The PCR-product and plasmid pA1 are digested with the restriction endonucleases Hind III and EcoR V and the PCR-product is ligated into the vector. The resulting plasmid is designated pA1: PTH(1–34)C-1C. The T7 expression cassette from pA1: PTH(1–34)C-1C is transferred to pBN1 by digesting both vectors with Xba I and BspE I, and subsequently ligating the approximately 1100 base pair fragment containing the expression cassette from pA1: PTH

```
Oligo 1: 5' CCC AAG CTT CTG TTC GTG GTC CGC GTT CTG TTT    (SEQ ID NO: 25)
            CTG AAA Oligo 2: 5' GAA ACA GAA CGC GGA CCA CGA ACA GAA GCT TGG G  (SEQ ID NO: 26)

Oligo 3: 5' TCC AGC TGA TGC ACA ACC TGG GTA AAC ACC TGA    (SEQ ID NO: 27)
            ACT Oligo 4: 5' AGG TGT TTA CCC AGG TTG TGC ATC AGC TGG ATT    (SEQ ID NO: 28)
            TCA Oligo 5: 5' CTA TGG AAC GTG TTG AAT GGC TGC GTA AAA AAC    (SEQ ID NO: 29)
            TGC A Oligo 6: 5' TTT TTT ACG CAG CCA TTC AAC ACG TTC CAT AGA    (SEQ ID NO: 30)
            GTT C Oligo 7: 5' GGA CGT TCA CAA CTT CTA AGA TAT CCG G          (SEQ ID NO: 31)

Oligo 8: 5' CCG GAT ATC TTA GAA GTT GTG AAC GTC CTG CAG    (SEQ ID NO: 32)
```

The eight synthetic DNA oligonucleotides were obtained and the complementary strands were phosphorylated and annealed. The four double stranded fragments were used to prepare a DNA fragment coding for the interpeptide linker followed by PTH(1–34) (SEQ ID NO:56). This DNA fragment was digested and inserted into pA1 using the restriction sites Hind III and EcoR V creating the vector pA1: PTH(1–34).

The expression cassette from pA1: PTH(1–34) was transferred to pBN1 (described above) by digesting both vectors with Xba I and BspE I and then ligating the approximately (1–34)C-1C into the pBN1. The resulting plasmid is designated pBN1: PTH(1–34)C-1C. FIG. 1 depicts a portion a the DNA sequence (and the corresponding peptide sequence) of pBN1: PTH(1–34)C-1C.

EXAMPLE 8

Expression Plasmids for PTH Multicopies Double Copy Construct

The plasmid pBN1: PTH(1–34)C-1C is digested with Sal I and BspE I and the fragment containing the DNA sequence coding for the thrombin site, the desired polypeptide, and the T7-terminator is purified. The fragment is then inserted into the plasmid pBN1: PTH(1–34)C-1C, which has been digested with Xho I and BspE I. The resulting plasmid is designated pBN1: PTH(1–34)C-2C. FIG. 2 shows a portion a the DNA sequence (and the corresponding peptide sequence) of pBN1: PTH(1–34)C-2C.

Four Copy Construct

The plasmid pBN1: PTH(1–34)C-2C is digested with Sal I and BspE I and the DNA sequence containing the thrombin site through the T7-terminator is purified. The fragment is then inserted into pBN1: PTH(1–34)C-2C which had been digested with Xho I and BspE I to yield pBN1: PTH(1–34) C-4C. Plasmids having higher numbers of copies of the PTH(1–34) (SEQ ID NO:56) sequence may be made using the same strategy.

EXAMPLE 9

Expression Plasmid for PTH Multicopy without hCAII

Multicopy constructs having at least 2 copies of the PTH(1–34) (SEQ ID NO:56) sequence may be expressed as inclusion bodies from a construct which does not contain hCAII sequence. For example, constructs including at least 2 copies of the PTH(1–34) (SEQ ID NO:56) sequence may be expressed.

The plasmid pBN1: PTH(1–34)C-$x_c$ (where x represents the number of copies of the PTH(1–34) (SEQ ID NO:56) sequence present in the plasmid) may be digested with Nco I and BspE I and ligated into the expression vector pBN5, which has also been digested with the same restriction endonucleases, to provide the plasmid pBN5: PTH(1–34)C-$x_c$.

Higher copy numbers may be made by digestion of plasmid pBN5: PTH(1–34)C-$y_c$ (where y represents the number of copies of the PTH(1–34) (SEQ ID NO:56) sequence present in the plasmid) with Sal I and BspE I, purifying the DNA fragment containing the multicopy gene and inserting the fragment into the plasmid pBN5: PTH (1–34)C-$x_c$ which had been digested with Xho I and BspE I. The resulting fragment is designated:

pBN5: PTH(1–34)C-$(x+y)_c$, where x+y represents the number of copies of the PTH (1–34) (SEQ ID NO:56) sequence present in the plasmid.

EXAMPLE 10

Production of PTH(1–34)-NH$_2$

Competent *E. coli* BL21 F$^-$ ompT $r^-_B$ $m^-_B$ (DE3) host cells may be transformed with plasmid pBN1: PTH(1–34) C-2C and cultured according to the procedures described in Examples 4 and 5 above. A portion of the nucleotide sequence which encodes two copies of PTH(1–34) (SEQ ID NO:56)and flanking sequences is shown in FIG. 2.

The transformed cells may be lysed and the inclusion bodies containing the hCA-PTH fusion protein construct isolated by centrifugation. The inclusion body pellet obtained from centrifugation is dissolved in 50 mM NaOH, and the pH was immediately reduced to 8.1 by the addition of 1M Tris-HCl. Thrombin is added (thrombin/construct weight ratio of 1 to 1500) and proteolysis is allowed to occur for 48 hours at 37° C. The reaction is terminated by rendering the solution 0.1 mM with respect to PMSF. In addition to cleaving the fragment containing hCAII (hCAII fragment) from the remainder of the construct, the thrombin treatment cleaves the multicopy portion of the construct into two pre-PTH fragments. Each pre-PTH fragment contains a single copy of PTH(1–34) (SEQ ID NO:56)flanked at the C-terminus by a cysteine residue (i.e., PTH(1–34)-Cys-Ttt where Ttt is a C-terminal tail sequence). The hCAII fragment is precipitated by rendering the solution 90 mM with respect to citric acid and the precipitate is removed by centrifugation. The pre-PTH fragments remain in the supernatant fluid.

Cyanylation/Amidation of the Pre-PTH Fragments

After desalting the supernatant by a low pressure C8 column, the pre-PTH fragments may be dissolved in a pH 3.5 urea/ammonium acetate buffer and treated with excess DTT and DMAP-CN at room temperature for 15–30 minutes. The reaction mixture is then immediately desalted, e.g., using an low pressure C8 column. The desalted S-derivatized fragments are then dissolved in 3M aqueous ammonia and allowed to react for 30 minutes at 0° C. to produce recombinant PTH(1–34)-NH$_2$ (SEQ ID NO:56). The PTH(1–34)-NH$_2$ (SEQ ID NO:56) may be further purified by HPLC on a semi-preparative C18 column using an acetonitrile gradient.

EXAMPLE 11

Expression Plasmids for GRF Single Copy

A GRF-construct was made consisting of a DNA segment coding for the hCAII, an interlinking peptide and GRF (1–44) (SEQ ID NO:57). An oligonucleotide coding for an inter-linking peptide sequence (FVNGPRAMVDDDDK) (SEQ ID NO:35) was substituted for the last three residues of hCAII, SFK. The double-stranded oligonucleotide for the product peptide sequence was inserted directly after the peptide linker region. The gene sequence of the inter-linking peptide region coded for a series of amino acids with unique sites that can either be processed chemically or by proteases to release the desired product peptide.

Oligonucleotides corresponding to segments of the linker and the peptide were obtained from the DNA Synthesis Core Facilities of the Interdisciplinary Center for Biotechnology at the University of Florida.

Modification of the hCAII Sequence

Eight oligonucleotides containing segments of the linker and the peptide were phosphorylated and complimentary oligonucleotide pairs 1&2, 3&4, 5&6, and 7&8 were annealed. Oligonucleotide pairs 1&2 and 3&4 were simultaneously joined into the pTZ19R vector (commercially available from Pharmacia Biotech Inc., NJ) between the Hind III and Sal I sites to yield pTZ: GRF(1–29). Oligonucleotide pairs 1&2 and 3&4 were simultaneously ligated into a separate pTZ19R vector between the Sal I and EcoR I sites to yield pTZ: GRF(29–44)A. The gene fragments were cloned adjacent to each other in a single vector by digesting pTZ: GRF(1–29) and pTZ: GRF(29–44)A with the restriction endonucleases Xmn I and Sal I, isolating the 1.9 kb band from the pTZ: GRF(1–29) vector and the 0.9 kb band from the pTZ: GRF(29–44)A and ligating them together to yield the vector pTZ: GRF(1–44)A.

The three Asn-Gly sites in hCAII (located at positions 10-11, 61-62, and 230-231) were changed to Gln10-Gly11, Gln61-Gly62 and Asn230-Ala231. The changes were made by site directed mutagenesis of specific codons in pA1. oligonucleotide containing the desired mutations for Asn61-Gly62 along with another primer to the carboxy end of hCAII were used to amplify the portion of the gene containing the sequence to be changed. The PCR fragment was digested with Hind III and BamH I and ligated into pA1 at the restriction sites mentioned above.

The Asn10-Gly11 and Asn230-Gly231 mutations were created using Amersham's Site Directed Mutagenesis Kit. The three oligonucleotide sequences are given below:

```
positions 10-11:   5' GGC AAA CAC CAG GGA CCT GAG CAC TG    (SEQ ID NO: 36)

positions 61-62:   5' CTG AGG ATC CTC AAC CAG GGT CAT GCT   (SEQ ID NO: 37)
                      TTC positions 230-231: 5' CTT AAC TTC AAT GCG GAG GGT GAA CC    (SEQ ID NO: 38)
```

All three mutations were combined to create the plasmid pA2. The pA2 vector was digested with EcoR V. PTZ: GRF was digested with Dra I and EcoR V. The fragment containing the GRF gene and the linearized pA2 plasmid were ligated together to yield pA2: GRF(1–44)A. Both pA2: GRF(1–44)A and pBN2 were digested with Xba I and BspE I. The expression cassette from the pA2: GRF(1–44)A was ligated into pBN1 to yield the final expression vector pBN2: GRF(1–44)A.

EXAMPLE 12

Expression Plasmids for GRF Multicopies

Plasmids containing nucleotide sequence coding for multiple copies of GRF fused to hCAII were prepared. The constructs contain an interlinking peptide between the individual copies of GRF. The interlinking peptide includes a cysteine residue and an enterokinase cleavage site. In front of the first copy of the peptide and downstream of the hCAII gene a linker which contains a thrombin cleavage site, a cysteine cleavage site and an enterokinase site, is inserted. This provides more flexibility in the purification of the product peptide.

A portion of the resulting construct is shown in FIG. 3. Construction af Single Copy Gene Six oligonucleotides were obtained from GENE LINK INC., 401 Clairmont Ave, Thornwood N.Y. 10594.

pUC19 (commercially available form NEW ENGLAND BIOLABS, Inc., 32 Tozer Road, Beverly Mass. 01915-5599) were digested with the restriction endonucleases Pst I and EcoR I. The PCR product was then ligated into the digested vector to yield pUC19: GRF(22–44)C.

The middle part of the gene construct was PCR-amplified where oligonucleotides 3 and 4 are overlapping primers that were filled in by the Taq polymerase during the thermocycling process. The PCR product and the vector pUC19: GRF(22–44)C were digested with the restriction endonucleases Pst I and Hind III. The PCR product was then ligated into the digested vector to yield pUC19: GRF(1–44)C.

The gene sequence for the interlinking peptide was modified as follows. The front part of the gene construct was PCR-amplified where oligonucleotides 5 and 6 are overlapping primers that are filled in by the Taq polymerase. The PCR product and the vector pUC19: GRF(1–44)C were digested with the restriction endonucleases Hind III and Sal I. The PCR product was then ligated into the digested vector to yield pUC19: GRF(1–44)C-$1_c$.

The gene sequence for the interlinking peptide and GRF construct was transferred from pUC19: GRF(1–44)C-$1_c$ to pA2 as follows. Plasmids pUC19: GRF(1–44)C-$1_c$ and pA2 were digested with Hind III and EcoR V and the DNA sequence for the interlinking peptide and the desired gene construct was purified and ligated into the pA2, which also was digested with the same restriction endonucleases. This yielded the vector pA2: GRF(1–44)C-$1_c$. This plasmid may be used for expression with ampicillin resistance.

The expression cassette of the pA2: GRF(1–44)C-$1_c$ was transferred to pBN1 by digestion of both pA2: GRF(1–44) C-$1_c$ and pBN1 with the restriction endonucleases Xba I and BspE I. The segment for the fusion protein was ligated into

```
Oligo 1: 5' TGC TGC AGG ACA TCA TGT CCC GTC AGC AGG GTG   (SEQ ID NO: 39)
            AAT CTA AC Oligo 2: 5' CCG AAT TCG ATA TCT TAC TCG AGC ATA GCG CAC   (SEQ ID NO: 40)
            AGA CGA GCA CGA GCA CC Oligo 3: 5' CAA AGC TTT CGC CAT GGT CGA CGA CGA CGA CAA   (SEQ ID NO: 41)
            ATA CGC TGA CGC TAT CTT CAC CAA CTC T Oligo 4: 5' GTC CTG CAG CAG TTT ACG AGC AGA CAG CTG ACC   (SEQ ID NO: 42)
            CAG AAC TTT ACG GTA AGA GTT GGT GAA Oligo 5: 5' CCA AAG CTT TCG GTG GTG GTG GTG GTC CGC GTG   (SEQ ID NO: 43)
            GT Oligo 6: 5' GTC GTC GAC CAT GGC GCA ACC ACG CGG ACC       (SEQ ID NO: 44)
```

A cysteine was inserted between the codon for the last amino acid in GRF and the stop codon. Additional restriction endonuclease sites Xho I, EcoR V and EcoR I site were inserted to ease the construction of the multicopy construct.

The last part of the gene construct was PCR-amplified using oligonucleotides 1 and 2 as primers and pBN2: GRF(1–44)A as a template. The PCR product and the vector the pBN1 to yield the final expression vector pBN2: GRF(1–44)C-$1_c$ (see FIG. 3 which depicts a portion of the plasmid).

Double Copy Construct

Figure 4B:
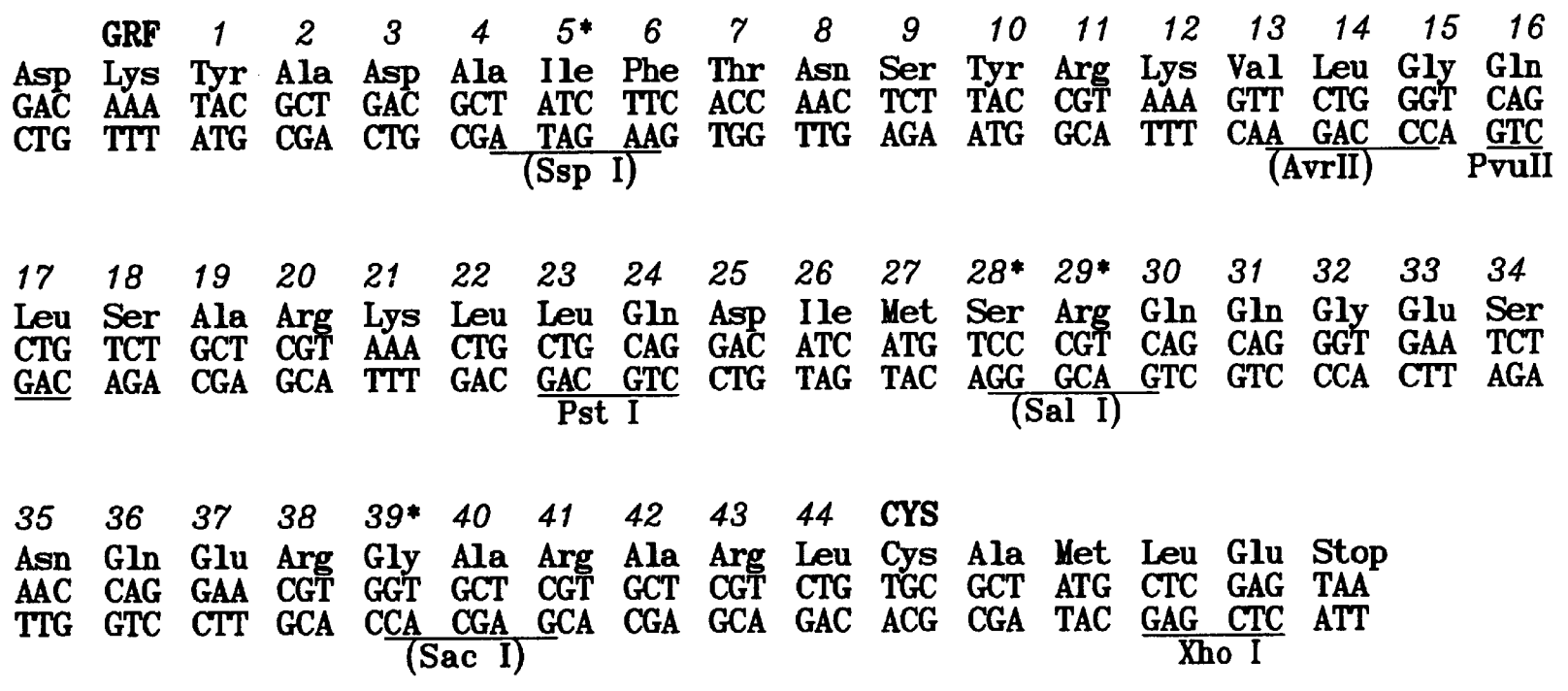

The plasmid pBN2: GRF(1–44)C-$1_c$ may be digested with Sal I and BspE I and the DNA fragment containing the enterokinase site, the GRF(1–44)C and the T7-terminator DNA sequence is purified. The fragment is then inserted into pBN2: GRF(1–44)C-1$_c$ which has been digested with Xho I and BspE I to yield pBN2: GRF(1–44)C-2$_c$ (see FIG. 4).

Four Copy Construct

The plasmid pBN2: GRF(1–44)C-2$_c$ may be digested with Sal I and BspE I and the DNA fragment containing the sequence coding for the enterokinase site, the desired peptide and the T7-terminator is purified. The fragment is then inserted into pBN2: GRF(1–44)C-2$_c$ which has been digested with Xho I and BspE I to yield pBN2: GRF(1–44) C-4$_c$.

EXAMPLE 13

Expression Plasmid for GRF Multicopy without hCAII

The plasmid pBN2: GRF(1–44)C-x$_c$ (where x represents the number of copies of the GRF sequence present in the plasmid) may be digested with Nco I and BspE I and ligated into the expression vector pBN5, which has also been digested with the same restriction endonucleases yielding the vector pBN5: GRF(1–44)C-x$_c$.

The number of copies of GRF(1–44) (SEQ ID NO:57) in a plasmid may be increased by digestion of plasmid pBN5: GRF(1–44)C-y$_c$ (where y represents the number of copies of the GRF sequence present in the plasmid) with Sal I and BspE I, purifying the DNA fragment containing the multicopy gene and inserting it into the plasmid pBN5: GRF (1–44)C-y$_c$, which had been digested with Xho I and BspE I, and ligating the purified fragments. The resulting plasmid is designated pBN5: GRF(1–44)C-(x+y)$_c$, where x+y represents the number of copies of the GRF sequence present in the plasmid.

EXAMPLE 14

Production of GRF(1–44)-NH$_2$ from a Multicopy Construct

Competent *E. coli* BL21 F$^-$ ompT r$^-_B$ m$^-_B$ (DE3) host cells may be transformed with the plasmid pBN2: GRF (1–44)C-4C and cultured according to the procedures described in Examples 4 and 5 above. The cells are lysed and the inclusion bodies containing the hCA-GRF fusion protein construct are isolated by centrifugation.

The frozen pellet from above (10 to 20 g) containing the fusion protein is added to 2 l of 50 mM NaOH containing 0.25 g N-lauryl-sarcosine. After being homogenized to insure complete dissolution, the pH is confirmed to be between 11.6 and 11.9. The solution is sonicated to insure that the last trace of pellet dissolved. At this point the protein concentration is between 12 and 15 mg/ml. The pH of the solution is then adjusted to 8.0 to 8.2 with 1 M Tris-HCl and the resulting solution filtered through a 0.45 μm membrane.

Thrombin may be added to the peptide at a weight ratio of 1 to 15,000, respectively. Proteolysis of the interlinking peptide is allowed to proceed at 37° C. for 22 to 24 hours. The reaction is terminated by rendering the solution 0.1 mM with respect to PMSF. The resulting solution may be used immediately or stored at −80° C.

The thrombin digested fusion protein is rendered 90 mM with respect to citric acid thereby causing the N-terminal fragment containing the hCAII peptide to precipitate. The protein precipitate may be removed by centrifugation. The supernatant containing the multicopy GRF fragment is filtered through a 0.45 μm filter.

The multicopy GRF fragment may be dissolved in a pH 3.5 urea/ammonium acetate buffer and treated with excess DMAP-CN (an S-cyanylating agent) at room temperature for 15–30 minutes. The reaction mixture is then immediately desalted, e.g., using an low pressure C8 column. The desalted, S-derivatized multicopy fragment may be dissolved in 3M aqueous ammonia and allowed to react for 30 minutes at room temperature to produce pre-GRF fragments. The pre-GRF fragments include the amino acid sequence DDDDK-GRF(1–44) -NH$_2$ (SEQ ID NO:58).

The solution of the pre-GRF fragments is diluted with H$_2$O to produce a peptide concentration of 1.0 mg/ml. Triton X-100 is added to a final concentration of 0.1%. Succinic acid and calcium chloride are added to produce concentrations of 50 mM (5.9 mg/ml) and 2 mM (0.3 mg/ml) respectively and the solution pH is adjusted to 5.5. After the solution is filtered through a 0.45 μm membrane, 5.0 mg/ml Dowex 1 resin is added. A 1:3000 ratio of enterokinase enzyme is added and the reaction is maintained in a 35–40° C. water bath with constant stirring. After 20–24 hours the cleavage reaction which converts the pre-GRF fragments into GRF(1–44)-NH2 (SEQ ID NO:57) reaches 70–80% completion. The reaction mixture is filtered to remove the Dowex 1 and the reaction is stopped by the addition of acetonitrile to a final concentration of 15%. The sample may be stored at −80° C. If desired, purification of the GRF (1–44)-NH$_2$ (SEQ ID NO:57). product may be carried out by preparative HPLC using a C8 column.

EXAMPLE 15

Expression Plasmid for GLP1(7–36) Multicopy Single Copy Construct

A GLP1(7–36) (SEQ ID NO:53)-construct was made consisting of a DNA segment coding for hCAII, an interlinking peptide and GLP1(7–36)-Cys-Ala (SEQ ID NO:63). The interlinking peptide included 5 glycine residues, a thrombin site (Gly-Pro-Arg), a cysteine residue and a cyanogen bromide cleavage site (in order running from the N-terminal to C-terminal). The permits more flexibility in the purification of the construct.

Four oligonucleotides were obtained from GENE LINK INC., 401 Clairmont Ave, Thornwood N.Y. 10594.

```
Oligo 1: 5' GTC AAA TTT GGC GGC CGC GGT GGT GGT GGT GGT (SEQ ID NO: 45)
            GTT AAC GGT CCG CGT GGT
```

```
Oligo 2: 5' GTC CTC GAG GGT ACC TTC AGC ATG CAT GTC GAC (SEQ ID NO: 46)
            AGC GCA ACC ACG CGG ACC G
```

```
                                    -continued
Oligo 3: 5' CTG GGT ACC TTC ACC TCC GAC GTT TCC TCC TAC (SEQ ID NO: 47)
            CTG GAA GGT CAG GCT GCT AAA GAA TTC Oligo 4: 5' CCT GGT CGA CTT ACT CGA GAG CGC AAC GAC CTT (SEQ ID NO: 48)
            TAA CCA GCC AAG CGA TGA ATT CTT TAG C
```

Oligonucleotides 1 and 2 are overlapping primers which were filled in with Taq polymerase during PCR amplification. The PCR product was digested with the restriction endonucleases Apo I and Xho I and inserted into the pBN4, which had been digested with EcoR I and Xho I. The resulting construct was designated pBN4: GLP(7–11)

Oligonucleotides 3 and 4 are also overlapping primers which were filled in with Taq polymerase during PCR amplification and the product was digested with Kpn I and Sal I, and ligated into pUC19, which also had been digested with Kpn I and Sal I yielding the construct pUC19: GLP (11–36)C. The pUC19: GLP(11–36)C was digested with Kpn I and Hinc II and inserted into a pA5 vector digested with Kpn I and EcoR V. The resulting vector pA5: GLP (11–36)C was digested with Kpn I and BspE I and the C-terminal backbone of the GLP construct followed by the T7 terminator was transferred into the pBN4: GLP(7–11) digested with Kpn I and BspE I which already contained the hCAII, the interlinking peptide sequence and the GLP(7–11) gene. The final vector was named pBN4: GLP(7–36)C-1$_c$ (see FIG. 5) and could be used for production of a single copy GLP fusion construct.

Double Copy Construct

The plasmid pBN4: GLP(7–36)C-1$_c$ may be digested with Sal I and BspE I and the DNA fragment containing the sequence for the cyanogen bromide site, the desired peptide and the T7-terminator is purified. The fragment is then inserted into pBN4: GLP(7–36)C-1$_c$, which has been digested with Xho I and BspE I to yield pBN4: GLP(7–36) C-2$_c$ (see FIG. 6).

Four Copy Construct

The plasmid pBN4: GLP(7–36)C-2$_c$ may be digested with Sal I and BspE I and the DNA fragment containing the sequence for the cyanogen bromide site, the desired peptide and the T7-terminator is purified. The fragment is then inserted into pBN4: GLP(7–36)C-2$_c$, which has been digested with Xho I and BspE I to yield pBN4: GLP(7–36) C-4$_c$.

Higher Copy Constructs

Plasmids having a greater number of copies of GLP(7–36) (SEQ ID NO:53) may be prepared by digesting plasmid pBN4: GLP(7–36)C-x$_c$ (where x is the number of copies of GLP in the plasmid) with Sal I and BspE I. The DNA sequence which includes the cyanogen bromide site, the desired peptide and the T7-terminator is purified. The purified fragment is then inserted into plasmid pBN4: GLP (7–36)C-y$_c$ (where y is the number of copies of GLP in the plasmid), which has been digested with Xho I and BspE I to yield plasmid pBN4: GLP(7–36)C-(x+y)$_c$ (where x+y is the number of copies of GLP in the plasmid). For example, plasmid pBN4: GLP(7–36)C-8$_c$ may be prepared using this method from pBN4: GLP(7–36)C-4$_c$ (i.e, where x and y are both 4).

EXAMPLE 16

Production of GLP1(7–36)-NH$_2$

Competent E. coli BL21 F$^-$ ompT r$^-$$_B$ m$^-$$_B$ (DE3) host cells may be transformed with plasmid pBN4: GLP(7–36) C-2C and cultured according to the procedures described in Examples 4 and 5 above. The cells are lysed and the inclusion bodies containing the hCA-GLP fusion protein construct are isolated by centrifugation.

The inclusion body pellet obtained from the centrifugation is suspended at a concentration of 90 g pellet per l in a buffer containing 2% N-lauryl sarcosine 25 mM Tris HCl, 50 mM EDTA, pH 7.6. The suspension is sonicated in 1 l aliquots for 4 minutes at room temperature.

The solution is centrifuged at 23,400×g for 10 minutes in Sorvall GSA rotor. The supernatant fluid is made 25% saturated ammonium sulfate by addition of solid, and after 3 hours at 4° C., the precipitate that formed is collected by centrifugation at 23,400×g for 10 minutes.

The pellets may be resuspended in 50% ethanol (2 l), then centrifuged at 23,400×g for 10 minutes to collect the pellet. This wash step is repeated once more with 2 l of 50% ethanol. The pellets are then suspended in the centrifuge bottles with 200 ml of 100 mM EDTA per bottle. After sitting for 10 mins, the suspensions are centrifuged at 15,000×g. This step is repeated once more with distilled H$_2$O in place of 100 mM EDTA. The resulting pellets were immediately used in the next step or stored frozen at −80° C.

The frozen pellet from above (10 to 20 g) containing the fusion protein is added to 2 l of 50 mM NaOH containing 0.25 g N-lauryl-sarcosine. After being homogenized to insure complete dissolution, the pH is confirmed to be between 11.6 and 11.9. The solution is sonicated to insure that the last trace of pellet dissolved. At this point the protein concentration is between 12 and 15 mg/ml. The pH of the solution is then adjusted to 8.0 to 8.2 with 1 M Tris-HCl and the resulting solution filtered through a 0.45 μm membrane.

Thrombin may be added to the peptide at a weight ratio of 1 to 15,000, respectively. Proteolysis of the interlinking peptide is allowed to proceed at 37° C. for 22 to 24 hours. The reaction is terminated by rendering the solution 0.1 mM with respect to PMSF. The resulting solution may be used immediately or stored at −80° C.

The thrombin digested fusion protein is rendered 90 mM with respect to citric acid thereby causing the N-terminal fragment containing the hCAII peptide to precipitate. The protein precipitate may be removed by centrifugation at 20,000×g and resuspended in 90 mM Na citrate, pH 3.0. The suspension is centrifuged again, and the supernatant fluid is combined with the first supernatant fluid. The combined supernatants containing the multicopy GLP fragment are filtered through a 0.45 μm filter and stored at −80° C. until used. The multicopy GLP fragment released from the fusion protein by the thrombin cleavage includes a 6 amino acid N-terminal tail sequence (Gly Cys Ala Val Asp Met) (SEQ ID NO:59). The two GLP1(7–36) (SEQ ID NO:53) sequences are flanked by an N-terminal methionine residue and a C-terminal Cys-Ala sequence.

The multicopy GLP fragment is absorbed onto a preparative C8 reverse phase column equilibrated with 10% ethanol in 10 mM acetic acid. The column is washed with the same solution, and the peptide eluted with 50% ethanol in 10 mM acetic acid. The solvent may be removed by rotavaporation to yield the desalted peptide product.

Cyanogen Bromide Cleavage of Multicopy GLP Fragment

The desalted multicopy GLP fragment may be dissolved in a 2M Citric Acid, pH 1.0 solution. Cyanogen bromide (CNBr) is added after purging the solution with Argon. After 4–5 hours of reaction the resulting pre-GLP fragments may be desalted using the procedure described above.

Cyanylation/Amidation of the Pre-GLP Fragments

The pre-GLP fragments may be dissolved in a pH 3.5 urea/ammonium acetate buffer and treated with excess DTT and DMAP-CN at room temperature for 15–30 minutes. The reaction mixture is then immediately desalted, e.g., using an low pressure C8 column or a Sephadex G-25 column. The desalted S-derivatized fragments are then dissolved in 3M aqueous ammonia and allowed to react for 30 minutes at room temperature to produce recombinant GLP1(7–36)-$NH_2$ (SEQ ID NO:53) (rGLP) The GLP1(7–36)-$NH_2$ (SEQ ID NO:53)may be further purified by HPLC on a semi-preparative C18 column using an acetonitrile gradient.

EXAMPLE 17

Production of GLP1(7–36)-$NH_2$ via CPD-Y Transamidation

Amidated recombinant GLP1(7–36)-$NH_2$ (SEQ ID NO:53)may be prepared from a recombinant multicopy fusion peptide by cleavage, transamidation and photochemical rearrangement.

A first DNA construct is formed by joining four copies of the coding sequence for GLPl(7–36)-Met (SEQ ID NO:60) joined end to end. The DNA construct also has a nucleotide sequence coding for a methionine residue joined immediately upsteam of the DNA sequence encoding GLP1(7–36)-Met (SEQ ID NO:60). This DNA construct may be formed by automated DNA synthesis and subcloned into the E. coli expression vector pBN1. A second DNA construct coding for a linking peptide which includes the thrombin cleavage site Gly-Pro-Arg is also subcloned into the resulting expression vector upstream from the first DNA construct. The expression vector may then be transformed into E. coli and the transformants selected and amplified. The multicopy fusion construct may be isolated as part of inclusion bodies from cell lysates as described in the Examples herein.

Treatment of the multicopy fusion construct with thrombin under the conditions described in Example 14 cleaves the hCAII peptide from the multi-GLP portion of the construct. The multicopy GLP peptide may be dissolved in 2M Citric Acid, pH 1.0 and cyanogen bromide (CNBr) added after purging the solution with Argon. The solution is permitted to react for 4–5 hours and the resulting fragments having the amino acid sequence GLP1(7–36)-Hse (SEQ ID NO:61) may be desalted on an low pressure C8 column.

The GLP1(7–36)-Hse (SEQ ID NO:61) fragments may be dissolved in 2 ml of 50 mM sodium carbonate buffer (pH 6.05) containing 1 mM EDTA and 250 mM (2-nitrophenyl) glycinamide (ONPGA). Reaction is initiated by the addition of a carboxypeptidase or a mutant of carboxypeptidase Y. The transamidation reaction provides the peptide GLP1 (7–36)-ONPGA (SEQ ID NO:61) which upon irradiation with UV light of a wavelength no shorter than 320 nm is converted into GLP1(7–36)-$NH_2$ (SEQ ID NO:53).

EXAMPLE 18

Production of GLP1(7–36)-$NH_2$ via CPD-Y Transpeptidation

The amidated recombinant peptide, GLP1(7–36)-$NH_2$ (SEQ ID NO:53), may also be prepared from a recombinant multicopy peptide by cleavage and transpeptidation.

The recombinant multicopy fusion peptide is produced by cells transformed with an expression vector. A first DNA construct is formed by joining four copies of the coding sequence for GLP1(7–35)-Met (SEQ ID NO:62) end to end. The DNA construct also has a nucleotide sequence coding for a methionine residue joined immediately upsteam of the DNA sequences encoding GLP1(7–35)-Met (SEQ ID NO:62). This DNA construct may be formed by automated DNA synthesis and subcloned into the expression vector pBN1. A second DNA construct coding for a linking peptide which includes the thrombin cleavage site Gly-Pro-Arg is also subcloned into the expression vector upstream from the first DNA construct. The expression vector may then be transformed into E. coli and the transformants are selected and amplified. The multicopy fusion construct may be isolated as part of inclusion bodies from cell lysates as described in the Examples herein.

Treatment of the multicopy fusion construct with thrombin as described in Example 14 cleaves the hCAII peptide from the multi-GLP portion of the construct (a multicopy GLP1(7–35)-Met peptide). The multicopy GLP1(7–35)-Met peptide may be cleaved in citric acid solution containing cyanogen bromide into fragments having the amino acid sequence GLP1(7–35)-Hse (SEQ ID NO:54). After desalting on an low pressure C8 column, the fragments may be transpeptidated by treatment with carboxypeptidase Y in a sodium carbonate buffer (pH 9.5) containing EDTA and the amidated amino acid, Arg-$NH_2$. The transpeptidation reaction yields GLP1(7–36)-$NH_2$ (SEQ ID NO:53) which, if desired, may be further purified on a C8 HPLC column.

EXAMPLE 19

Expression Plasmid for GLP1 Multicopy without hCAII

The following two synthetic DNA strands were prepared:

```
Oligo E: 5' A GGC GGC ATG GTC GGC GGC GGC GAC ATG CAT GCT      (SEQ ID NO: 49)
             GAA GG Oligo F: 5' CCT GGT CGA CTT ACT CGA GAG CGC AAC GAC CTT TAA    (SEQ ID NO: 50)
             CCA GCC AAG CGA TGA ATT CTT TAG C
```

The plasmid pBN4: GLP(7–36)C-1C was PCR-amplified using oligonucleotides E and F as primers. The PCR product was purified and digested with the restriction endonucleases Nco I and Xho I and ligated into the Nco I and Xho I digested expression vector pBN5. The resulting vector was designated pBN5: GLP(7–36)C-1C.

Multicopy GLP may be made by digestion of plasmid pBN5: GLP(7–36)C-$x_c$ (where x represents the number of copies of the GLP sequence present in the plasmid) and purification of the DNA fragment containing the multicopy gene and and the T7 terminator sequence. The fragment is inserted into the digested plasmid pBN5: GLP(7–36)C-1C. The resulting expression vector is designated pBN5: GLP (7–36)C-(x+1)C, where x+1 represents the number of copies of the GLP sequence present in the plasmid.

Purification of the Recombinant Multicopy PolypePtides

A variety of methods for purification of a recombinant multicopy peptide are known in the art. Suitable purification methods are described, for example, in Kirshner et al., *J. Biotechnology*, 12: 247–260 (1989) and Oldenburg et al., *Prot.Expr.Purif.*, 5, 278 (1994), the disclosure of which is incorporated herein by reference.

Therapeutic Use of Recombinant Modified Polypeptide Products Produced by the Method of the Invention The products of the present invention have significant therapeutic and supplemental physiological uses in clinical human and veterinary medical practice. For example, the insulinotrophic activity of GLP1(7–36)-$NH_2$ (SEQ ID NO:53) has been shown to be beneficial in treating the symptoms of non-insulin dependent diabetes mellitus (NIDDM, Type II). Gutniak, *New Eng. J. Med.*, 326: 1316–2 (1992). GRF(1–44)-$NH_2$ is of therapeutic benefit for diseases such as short stature syndrome, endometriosis, and osteoporosis. In addition, supplemental GRF has been used to increase the lean to fat ratio in livestock allowing production of more wholesome meat products.

Methods of preparation of pharmaceutically functional compositions of the products of the invention, in combination with a physiologically acceptable carrier, are known in the art. A functional pharmaceutical composition must be administered in an effective amount, by known routes of administration. The dosage at which the functional pharmaceutical composition is applied is dependent on purpose for its use and the condition of the recipient.

The invention has been described with reference to various specific and preferred embodiments and techniques. However, It will be apparent to one of ordinary skill in the art that many variations and modifications may be made while remaining within the spirit and scope of the invention.

All publications and patent applications in this specification are indicative of the level of ordinary skill in the art to which this invention pertains. All publications and patent applications are herein incorporated by reference to the same extent as if each individual publication or patent application was specifically and individually indicated by reference.

TABLE 2

Code Names for Plasmids

| Plasmid Name | hCA | Mutations to hCA | Cloning Sites at C-terminus of hCA | Restriction Sites That Were Delted Other Than During Cloning Procedure |
|---|---|---|---|---|
| pA1 | Yes | None | Hind III/EcoR V | — |
| pA2 | Yes | N10Q, N61Q, 6231A | Hind III/EcoR V | — |
| pA3 | Yes | None | EcoR I/Xho I | EcoR I from pBR 322 |
| pBN1 | Yes | None | Hind III/EcoR V | — |
| pBN2 | Yes | N10Q, N61Q, G231A | Hind III/EcoR V | — |
| pBN3 | Yes | None | Hind III/EcoR V | EcoR I from pBR 322 |
| pBN4 | Yes | None | EcoR I/Xho I | EcoR I from pBR3 |
| pBN5 | No | — | — | — |
| pA4 | Yes | M240C | Hind III/EcoR V | — |
| pA5 | Yes | None | Hind III/Kpn I/ EcoR V | — |
| pBN6 | Yes | M240C | Hind III/EcoR V | — |

What is claimed is:

1. A method of producing a peptide having a C-terminal α-carboxamide comprising:

converting a recombinant protein construct to a product peptide having a C-terminal α-carboxamide by contact of the recombinant protein construct with (a) an S-cyanylating agent and an amine compound, and (b) a CS1 cleaving agent; wherein, the recombinant protein construct has an amino acid sequence of the formula:

Yyy-TargP-Cys-(-(Ln1)$_n$-(CS1)-TargP-Cys-)$_r$-Xxx

-CS1- is a chemical cleavage site selected from the group consisting of AspGly, AspPro, AsnGly, Met and Trp;

the CS1 cleaving agent is low pH for AspGly and AspPro, hydroxylanine for AsnGly, cyanogen bromide for Met, and BNPS-skatole or other oxidizing agent for Trp;

-(Ln1)- is a linking peptide other than CS1, Cys or TargP, and is a spacer unit;

-TargP- is a target peptide which is free of unblocked cysteine residues;

n is 0 or 1;

r is an integer from 1 to about 150;

Yyy- is a leader group and includes a cleavage site at its C end;

-Xxx is a tail group; and steps (a) and (b) are carried out either in an order—a followed by b or an order—b followed by a.

2. The method of claim 1 wherein the target peptide includes an amino acid sequence corresponding to a peptide selected from the group consisting of GLP1(7–36) (SEQ ID NO:53), GRF(1–44) (SEQ ID NO:57), PTH(1–34) (SEQ ID NO:56) and substance P.

3. The method of claim 1 wherein the target peptide includes a methionine residue; and the step of converting includes cleaving at the -(CS1)- cleavage site and the cleaving step does not include contacting the -(CS1)- cleavage site with cyanogen bromide.

4. The method of claim 3 wherein the target peptide includes an amino acid sequence corresponding to a peptide selected from the group consisting of GRF(1–44) (SEQ ID NO:57) and PTH(1–34) (SEQ ID NO:56).

5. The method of claim 1 wherein the S-cyanylating agent includes thiocyanato substituted aromatic compound.

6. The method of claim 1 wherein the S-cyanylating agent includes 1-cyano-4-(dialkylamino)pyridinium salt.

7. The method of claim 1 wherein the target peptide is free of methionine residues; the -(CS1)- cleavage site is a methionine residue; and the step of converting includes contacting the -(CS1)- cleavage site with cyanogen bromide to cleave the C-terminal peptide bond of the methionine residue.

8. The method of claim 7 wherein the target peptide includes an amino acid sequence corresponding to GLP1 (7–36) (SEQ ID NO:53).

9. The method of claim 1 wherein the step of converting includes contacting the -(CS1)- cleavage site with a chemical cleavage agent to produce an intermediate peptide which includes -Cys-; contacting the intermediate peptide with the S-cyanylating agent to form an S-derivatized -Cys-; and reacting the S-derivatized -Cys- with the amino compound to produce the product peptide.

10. The method of claim 1 wherein the step of converting includes contacting the -Cys- with the S-cyanylating agent to form an S-derivatized -Cys-; reacting the S-derivatized -Cys- with the amino compound to form an intermediate peptide which includes the -(CS1)- cleavage site; and contacting the intermediate peptide with the chemical cleavage agent to produce the product peptide.

11. A method of producing a peptide having a C-terminal α-carboxamide comprising:
  i) expressing a recombinant protein construct in a host cell, wherein the recombinant protein construct includes an amino acid sequence having the formula:

Yyy-TargP-Cys-(-(Ln1)$_n$-(CS1)-TargP-Cys-)$_r$-Xxx

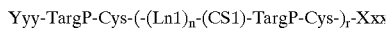

-CS1- is a chemical cleavage site selected from the group consisting of AspGly, AspPro, AsnGly, Met and Trp;
  -(Ln1)- is a linking peptide other than CS1, Cys or TargP, and is a spacer unit;
  -TargP- is a target peptide which is free of unblocked cysteine residues;
  n is 0 or 1;
  r is an integer from 1 to about 150;
  Yyy- is a leader group and includes a cleavage site at its C end;
  -Xxx is a tail group;
  ii) isolating the recombinant protein construct; and
  iii) converting the recombinant protein construct to a product peptide having a C-terminal α-carboxamide by contact of the recombinant protein construct with (a) an S-cyanylating agent and an amine compound, and (b) a CS1 cleaving agent;
  steps (a) and (b) are carried out either in an order—a followed by b, or an order—b followed by a; and
  the CS1 cleaving agent is low pH for AspBly and AspPro, hydroxylamine for AsnGly, cyanogen bromide for Met, and BNPS-skatole or other oxidizing agent for Trp.

12. A recombinant protein construct having the formula:

Yyy-TargP-Cys-(-(Ln1)$_n$-(CS1)-TargP-Cys-)$_r$-Xxx

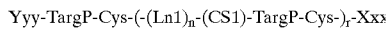

-CS1- is a chemical cleavage site selected from the group consisting of AspGly, AspPro, AsnGly, Met and Trp;
-(Ln1)- is a linking peptide other than CS1, Cys or TargP, and is a spacer unit;
-TargP- is a target peptide which is free of unblocked cysleine residues;
n is 0 or 1;
r is an integer from 1 to about 150;
Yyy- is a leader group and includes a cleavage site at its C end; and
-Xxx is a tail group.

13. A recombinant are containing a DNA sequence coding for a peptide which includes an amino acid sequence having the formula:

Yyy-TargP-Cys-[-(Ln1)$_n$-(CS1)-TargP-Cys-]$_r$-Xxx

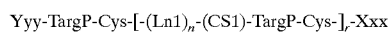

-CS1- is a chemical cleavage site selected from the group consisting of AspGly, AspPro, AsnGly, Met and Trp;
-(Ln1)- is a linking peptide other than CS1, Cys or TarP, and is a spacer unit;
-TargP- is a target pepide which is free of unblocked cysteine residues;
n is 0 or 1;
r is an integer from 1 to about 150;
Yyy- is a leader group and includes a cleavage site at its C end; and
-Xxx is a tail group.

* * * * *

SEQUENCE LISTING (1) GENERAL INFORMATION:

(iii) NUMBER OF SEQUENCES: 63

(2) INFORMATION FOR SEQ ID NO:1:

(i) SEQUENCE CHARACTERISTICS:
      (A) LENGTH: 168 base pairs
      (B) TYPE: nucleic acid
      (C) STRANDEDNESS: double
      (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
      (A) NAME/KEY: Coding Sequence
      (B) LOCATION: 1...159
      (D) OTHER INFORMATION:
      (A) NAME/KEY: mat_peptide
      (B) LOCATION: 1...53
      (D) OTHER INFORMATION:

(xi) SEQUENCE DESCRIPTION: SEQ ID NO:1:

ATC AAA GCT TCT GCC ATG GGC GGC CGC GTC GAC CGT GGT CCG CGT TCT   48

```
Ile Lys Ala Ser Ala Met Gly Gly Arg Val Asp Arg Gly Pro Arg Ser
 1               5                  10                 15

GTT TCT GAA ATC CAG CTG ATG CAC AAC CTG GGT AAA CAC CTG AAC TCT        96
Val Ser Glu Ile Gln Leu Met His Asn Leu Gly Lys His Leu Asn Ser
             20                  25                  30

ATG GAA CGT GTT GAA TGG CTG CGT AAA AAA CTG CAG GAC GTT CAC AAC       144
Met Glu Arg Val Glu Trp Leu Arg Lys Lys Leu Gln Asp Val His Asn
         35                  40                  45

TTC TGC GCT CTC GAG TAAGATATC                                         168
Phe Cys Ala Leu Glu
     50

(2) INFORMATION FOR SEQ ID NO:2:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: C-terminal (vi) ORIGINAL SOURCE:

(xi) SEQUENCE DESCRIPTION: SEQ ID NO:2:

Ile Lys Ala Ser Ala Met Gly Gly Arg Val Asp Arg Gly Pro Arg Ser
 1               5                  10                 15

Val Ser Glu Ile Gln Leu Met His Asn Leu Gly Lys His Leu Asn Ser
             20                  25                  30

Met Glu Arg Val Glu Trp Leu Arg Lys Lys Leu Gln Asp Val His Asn
         35                  40                  45

Phe Cys Ala Leu Glu
     50

(2) INFORMATION FOR SEQ ID NO:3:

(i) SEQUENCE CHARACTERISTICS:
        (A) LENGTH: 294 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...285
        (D) OTHER INFORMATION:
        (A) NAME/KEY: mat_peptide
        (B) LOCATION: 1...95
        (D) OTHER INFORMATION:

(xi) SEQUENCE DESCRIPTION: SEQ ID NO:3:

ATC AAA GCT TCT GCC ATG GGC GGC CGC GTC GAC CGT GGT CCG CGT TCT        48
Ile Lys Ala Ser Ala Met Gly Gly Arg Val Asp Arg Gly Pro Arg Ser
```

-continued

```
  1              5                10                15
GTT TCT GAA ATC CAG CTG ATG CAC AAC CTG GGT AAA CAC CTG AAC TCT       96
Val Ser Glu Ile Gln Leu Met His Asn Leu Gly Lys His Leu Asn Ser
             20                25                30

ATG GAA CGT GTT GAA TGG CTG CGT AAA AAA CTG CAG GAC GTT CAC AAC      144
Met Glu Arg Val Glu Trp Leu Arg Lys Lys Leu Gln Asp Val His Asn
         35                40                45

TTC TGC GCT CTC GAC CGT GGT CCG GCT TCT GTT TCT GAA ATC CAG CTG      192
Phe Cys Ala Leu Asp Arg Gly Pro Ala Ser Val Ser Glu Ile Gln Leu
     50                55                60

ATG CAC AAC CTG GGT AAA CAC CTG AAC TCT ATG GAA CGT GTT GAA TGG      240
Met His Asn Leu Gly Lys His Leu Asn Ser Met Glu Arg Val Glu Trp
 65                70                75                80

CTG CGT AAA AAA CTG CAG GAC GTT CAC AAC TTC TGC GCT CTC GAG TAAGAT   291
Leu Arg Lys Lys Leu Gln Asp Val His Asn Phe Cys Ala Leu Glu
                 85                90                95

ATC                                                                  294
```

(2) INFORMATION FOR SEQ ID NO:4:

(i) SEQUENCE CHARACTERISTICS:
        (A) LENGTH: 95 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: C-terminal (vi) ORIGINAL SOURCE:

(xi) SEQUENCE DESCRIPTION: SEQ ID NO:4:

```
Ile Lys Ala Ser Ala Met Gly Gly Arg Val Asp Arg Gly Pro Arg Ser
 1               5                10                15

Val Ser Glu Ile Gln Leu Met His Asn Leu Gly Lys His Leu Asn Ser
             20                25                30

Met Glu Arg Val Glu Trp Leu Arg Lys Lys Leu Gln Asp Val His Asn
         35                40                45

Phe Cys Ala Leu Asp Arg Gly Pro Ala Ser Val Ser Glu Ile Gln Leu
     50                55                60

Met His Asn Leu Gly Lys His Leu Asn Ser Met Glu Arg Val Glu Trp
 65                70                75                80

Leu Arg Lys Lys Leu Gln Asp Val His Asn Phe Cys Ala Leu Glu
                 85                90                95
```

(2) INFORMATION FOR SEQ ID NO:5:

(i) SEQUENCE CHARACTERISTICS:
        (A) LENGTH: 224 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
    (A) NAME/KEY: Coding Sequence
    (B) LOCATION: 1...207
    (D) OTHER INFORMATION:
    (A) NAME/KEY: mat_peptide
    (B) LOCATION: 1...69
    (D) OTHER INFORMATION:

(xi) SEQUENCE DESCRIPTION: SEQ ID NO:5:

```
AAA GCT TTC GGT GGT GGT GGT GGT CCG CGT GGT TGC GCC ATG GTC GAC        48
Lys Ala Phe Gly Gly Gly Gly Gly Pro Arg Gly Cys Ala Met Val Asp
 1               5                  10                  15

GAC GAC GAC AAA TAC GCT GAC GCT ATC TTC ACC AAC TCT TAC CGT AAA        96
Asp Asp Asp Lys Tyr Ala Asp Ala Ile Phe Thr Asn Ser Tyr Arg Lys
             20                  25                  30

GTT CTG GGT CAG CTG TCT GCT CGT AAA CTG CTG CAG GAC ATC ATG TCC       144
Val Leu Gly Gln Leu Ser Ala Arg Lys Leu Leu Gln Asp Ile Met Ser
         35                  40                  45

CGT CAG CAG GGT GAA TCT AAC CAG GAA CGT GGT GCT CGT GCT CGT CTG       192
Arg Gln Gln Gly Glu Ser Asn Gln Glu Arg Gly Ala Arg Ala Arg Leu
 50                  55                  60

TGC GCT ATG CTC GAG TAAGATATCG AATTCGG                                224
Cys Ala Met Leu Glu
 65
```

(2) INFORMATION FOR SEQ ID NO:6:

(i) SEQUENCE CHARACTERISTICS:
        (A) LENGTH: 69 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: C-terminal (vi) ORIGINAL SOURCE:

(xi) SEQUENCE DESCRIPTION: SEQ ID NO:6:

```
Lys Ala Phe Gly Gly Gly Gly Gly Pro Arg Gly Cys Ala Met Val Asp
 1               5                  10                  15

Asp Asp Asp Lys Tyr Ala Asp Ala Ile Phe Thr Asn Ser Tyr Arg Lys
             20                  25                  30

Val Leu Gly Gln Leu Ser Ala Arg Lys Leu Leu Gln Asp Ile Met Ser
         35                  40                  45

Arg Gln Gln Gly Glu Ser Asn Gln Glu Arg Gly Ala Arg Ala Arg Leu
 50                  55                  60

Cys Ala Met Leu Glu
 65
```

(2) INFORMATION FOR SEQ ID NO:7:

(i) SEQUENCE CHARACTERISTICS:
        (A) LENGTH: 369 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
(A) NAME/KEY: Coding Sequence
(B) LOCATION: 1...366
(D) OTHER INFORMATION:
(A) NAME/KEY: mat_peptide
(B) LOCATION: 1...122
(D) OTHER INFORMATION:

(xi) SEQUENCE DESCRIPTION: SEQ ID NO:7:

| | | | | | | | | | | | | | | | | |
|---|---|---|---|---|---|---|---|---|---|---|---|---|---|---|---|---|
| AAA | GCT | TTC | GGT | GGT | GGT | GGT | GGT | CCG | CGT | GGT | TGC | GCC | ATG | GTC | GAC | 48 |
| Lys | Ala | Phe | Gly | Gly | Gly | Gly | Gly | Pro | Arg | Gly | Cys | Ala | Met | Val | Asp | |
| 1 | | | | 5 | | | | | 10 | | | | | 15 | | |
| GAC | GAC | GAC | AAA | TAC | GCT | GAC | GCT | ATC | TTC | ACC | AAC | TCT | TAC | CGT | AAA | 96 |
| Asp | Asp | Asp | Lys | Tyr | Ala | Asp | Ala | Ile | Phe | Thr | Asn | Ser | Tyr | Arg | Lys | |
| | | | 20 | | | | 25 | | | | | 30 | | | | |
| GTT | CTG | GGT | CAG | CTG | TCT | GCT | CGT | AAA | CTG | CTG | CAG | GAC | ATC | ATG | TCC | 144 |
| Val | Leu | Gly | Gln | Leu | Ser | Ala | Arg | Lys | Leu | Leu | Gln | Asp | Ile | Met | Ser | |
| | | | 35 | | | | | 40 | | | | | 45 | | | |
| CGT | CAG | CAG | GGT | GAA | TCT | AAC | CAG | GAA | CGT | GGT | GCT | CGT | GCT | CGT | CTG | 192 |
| Arg | Gln | Gln | Gly | Glu | Ser | Asn | Gln | Glu | Arg | Gly | Ala | Arg | Ala | Arg | Leu | |
| | 50 | | | | | 55 | | | | | 60 | | | | | |
| TGC | GCT | ATG | CTC | GAC | GAC | GAC | AAA | TAC | GCT | GAC | GCT | ATC | TTC | ACC | | 240 |
| Cys | Ala | Met | Leu | Asp | Asp | Asp | Lys | Tyr | Ala | Asp | Ala | Ile | Phe | Thr | | |
| 65 | | | | | 70 | | | | | 75 | | | | | 80 | |
| AAC | TCT | TAC | CGT | AAA | GTT | CTG | GGT | CAG | CTG | TCT | GCT | CGT | AAA | CTG | CTG | 288 |
| Asn | Ser | Tyr | Arg | Lys | Val | Leu | Gly | Gln | Leu | Ser | Ala | Arg | Lys | Leu | Leu | |
| | | | | 85 | | | | | 90 | | | | | 95 | | |
| CAG | GAC | ATC | ATG | TCC | CGT | CAG | CAG | GGT | GAA | TCT | AAC | CAG | GAA | CGT | GGT | 336 |
| Gln | Asp | Ile | Met | Ser | Arg | Gln | Gln | Gly | Glu | Ser | Asn | Gln | Glu | Arg | Gly | |
| | | | | 100 | | | | | 105 | | | | | 110 | | |
| GCT | CGT | GCT | CGT | CTG | TGC | GCT | ATG | CTC | GAG | TAA | | | | | | 369 |
| Ala | Arg | Ala | Arg | Leu | Cys | Ala | Met | Leu | Glu | | | | | | | |
| | | | 115 | | | | | 120 | | | | | | | | |

(2) INFORMATION FOR SEQ ID NO:8:

(i) SEQUENCE CHARACTERISTICS:
(A) LENGTH: 122 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: C-terminal (vi) ORIGINAL SOURCE:

(xi) SEQUENCE DESCRIPTION: SEQ ID NO:8:

Lys Ala Phe Gly Gly Gly Gly Gly Pro Arg Gly Cys Ala Met Val Asp
1               5                   10                  15

Asp Asp Asp Lys Tyr Ala Asp Ala Ile Phe Thr Asn Ser Tyr Arg Lys
            20                  25                  30

Val Leu Gly Gln Leu Ser Ala Arg Lys Leu Leu Gln Asp Ile Met Ser

```
                35                    40                    45
Arg Gln Gln Gly Glu Ser Asn Gln Glu Arg Gly Ala Arg Ala Arg Leu
     50                    55                    60

Cys Ala Met Leu Asp Asp Asp Lys Tyr Ala Asp Ala Ile Phe Thr
 65                    70                    75                    80

Asn Ser Tyr Arg Lys Val Leu Gly Gln Leu Ser Ala Arg Lys Leu Leu
                85                    90                    95

Gln Asp Ile Met Ser Arg Gln Gln Gly Glu Ser Asn Gln Glu Arg Gly
                100                   105                   110

Ala Arg Ala Arg Leu Cys Ala Met Leu Glu
            115                   120
```

(2) INFORMATION FOR SEQ ID NO:9:

(i) SEQUENCE CHARACTERISTICS:
        (A) LENGTH: 174 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...165
        (D) OTHER INFORMATION:
        (A) NAME/KEY: mat_peptide
        (B) LOCATION: 1...55
        (D) OTHER INFORMATION:

(xi) SEQUENCE DESCRIPTION: SEQ ID NO:9:

```
GAA TTT GGC GGC CGC GGT GGT GGT GGT GGT GTT AAC GGT CCG CGT GGT      48
Glu Phe Gly Gly Arg Gly Gly Gly Gly Gly Val Asn Gly Pro Arg Gly
 1               5                   10                  15

TGC GCT GTC GAC ATG CAT GCT GAA GGT ACC TTC ACC TCC GAC GTT TCC      96
Cys Ala Val Asp Met His Ala Glu Gly Thr Phe Thr Ser Asp Val Ser
            20                  25                  30

TCC TAC CTG GAA GGT CAG GCT GCT AAA GAA TTC ATC GCT TGG CTG GTT     144
Ser Tyr Leu Glu Gly Gln Ala Ala Lys Glu Phe Ile Ala Trp Leu Val
        35                  40                  45

AAA GGT CGT TGC GCT CTC GAG TAAGTCGAC                               174
Lys Gly Arg Cys Ala Leu Glu
 50                  55
```

(2) INFORMATION FOR SEQ ID NO:10:

(i) SEQUENCE CHARACTERISTICS:
        (A) LENGTH: 55 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: C-terminal (vi) ORIGINAL SOURCE:

(xi) SEQUENCE DESCRIPTION: SEQ ID NO:10:

Glu Phe Gly Gly Arg Gly Gly Gly Gly Val Asn Gly Pro Arg Gly
 1               5                  10                  15

Cys Ala Val Asp Met His Ala Glu Gly Thr Phe Thr Ser Asp Val Ser
                20                  25                  30

Ser Tyr Leu Glu Gly Gln Ala Ala Lys Glu Phe Ile Ala Trp Leu Val
            35                  40                  45

Lys Gly Arg Cys Ala Leu Glu
 50                  55

(2) INFORMATION FOR SEQ ID NO:11:

(i) SEQUENCE CHARACTERISTICS:
        (A) LENGTH: 279 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...270
        (D) OTHER INFORMATION:
        (A) NAME/KEY: mat_peptide
        (B) LOCATION: 1...90
        (D) OTHER INFORMATION:

(xi) SEQUENCE DESCRIPTION: SEQ ID NO:11:

GAA TTT GGC GGC CGC GGT GGT GGT GGT GGT GTT AAC GGT CCG CGT GGT         48
Glu Phe Gly Gly Arg Gly Gly Gly Gly Gly Val Asn Gly Pro Arg Gly
 1               5                  10                  15

TGC GCT GTC GAC ATG CAT GCT GAA GGT ACC TTC ACC TCC GAC GTT TCC         96
Cys Ala Val Asp Met His Ala Glu Gly Thr Phe Thr Ser Asp Val Ser
                20                  25                  30

TCC TAC CTG GAA GGT CAG GCT GCT AAA GAA TTC ATC GCT TGG CTG GTT        144
Ser Tyr Leu Glu Gly Gln Ala Ala Lys Glu Phe Ile Ala Trp Leu Val
            35                  40                  45

AAA GGT CGT TGC GCT CTC GAC ATG CAT GCT GAA GGT ACC TTC ACC TCC        192
Lys Gly Arg Cys Ala Leu Asp Met His Ala Glu Gly Thr Phe Thr Ser
 50                  55                  60

GAC GTT TCC TCC TAC CTG GAA GGT CAG GCT GCT AAA GAA TTC ATC GCT        240
Asp Val Ser Ser Tyr Leu Glu Gly Gln Ala Ala Lys Glu Phe Ile Ala
 65                  70                  75                  80

TGG CTG GTT AAA GGT CGT TGC GCT CTC GAG TAAGTCGAC                      279
Trp Leu Val Lys Gly Arg Cys Ala Leu Glu
                    85                  90

(2) INFORMATION FOR SEQ ID NO:12:

(i) SEQUENCE CHARACTERISTICS:
        (A) LENGTH: 90 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: C-terminal (vi) ORIGINAL SOURCE:

(xi) SEQUENCE DESCRIPTION: SEQ ID NO:12:

```
Glu Phe Gly Gly Arg Gly Gly Gly Val Asn Gly Pro Arg Gly
 1               5                  10                  15

Cys Ala Val Asp Met His Ala Glu Gly Thr Phe Thr Ser Asp Val Ser
                20                  25                  30

Ser Tyr Leu Glu Gly Gln Ala Ala Lys Glu Phe Ile Ala Trp Leu Val
            35                  40                  45

Lys Gly Arg Cys Ala Leu Asp Met His Ala Glu Gly Thr Phe Thr Ser
        50                  55                  60

Asp Val Ser Ser Tyr Leu Glu Gly Gln Ala Ala Lys Glu Phe Ile Ala
65                  70                  75                  80

Trp Leu Val Lys Gly Arg Cys Ala Leu Glu
                85                  90
```

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
        (A) NAME/KEY: Coding Sequence
        (B) LOCATION: 1...15
        (D) OTHER INFORMATION:
        (A) NAME/KEY: mat_peptide
        (B) LOCATION: 1...5
        (D) OTHER INFORMATION:

(xi) SEQUENCE DESCRIPTION: SEQ ID NO:13:

```
GAC GAC GAC GAT AAA                                            15
Asp Asp Asp Asp Lys
 1               5
```

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:14:

Asp Asp Asp Asp Lys
1               5

(2) INFORMATION FOR SEQ ID NO:15:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(ix) FEATURE:
            (A) NAME/KEY: Coding Sequence
            (B) LOCATION: 1...12
            (D) OTHER INFORMATION:
            (A) NAME/KEY: mat_peptide
            (B) LOCATION: 1...4
            (D) OTHER INFORMATION:

(xi) SEQUENCE DESCRIPTION: SEQ ID NO:15:

ATT GAA GGA AGA                                                          12
Ile Glu Gly Arg
1

(2) INFORMATION FOR SEQ ID NO:16:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:16:

Ile Glu Gly A rg
1

(2) INFORMATION FOR SEQ ID NO:17:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO

```
        (v) FRAGMENT TYPE:

(vi) ORIGINAL SOURCE:

(ix) FEATURE:
              (A) NAME/KEY: Coding Sequence
              (B) LOCATION: 1...24
              (D) OTHER INFORMATION:
              (A) NAME/KEY: mat_peptide
              (B) LOCATION: 1...8
              (D) OTHER INFORMATION:

(xi) SEQUENCE DESCRIPTION: SEQ ID NO:17:

CAT CCT TTT CAT CTG CTG GTT TAT                                            24
His Pro Phe His Leu Leu Val Tyr
1               5

(2) INFORMATION FOR SEQ ID NO:18:

(i) SEQUENCE CHARACTERISTICS:
              (A) LENGTH: 8 amino acids
              (B) TYPE: amino acid
              (C) STRANDEDNESS: single
              (D) TOPOLOGY: linear (ii) MOLECULE TYPE: protein (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:18:

His Pro Phe His Leu Leu Val T yr
  1               5

(2) INFORMATION FOR SEQ ID NO:19:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:19:

AGCTTTCGTT GACGACGACG ATATCTT                                              27

(2) INFORMATION FOR SEQ ID NO:20:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: Genomic DNA (iii) HYPOTHETICAL: NO (iv) ANTI-SENSE: NO
```

(v) FRAGMENT TYPE:

(vi) ORIGINAL SOURCE:

(xi) SEQUENCE DESCRIPTION: SEQ ID NO:20:

AGCTAAGATA TCGTCGTCGT CAACGAA                                              27

(2) INFORMATION FOR SEQ ID NO:21:

(i) SEQUENCE CHARACTERISTICS:
                 (A) LENGTH: 25 base pairs
                 (B) TYPE: nucleic acid
                 (C) STRANDEDNESS: single
                 (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:21:

AGCTGAATTC AACGTTCTCG AGGAT                                                25

(2) INFORMATION FOR SEQ ID NO:22:

(i) SEQUENCE CHARACTERISTICS:
                 (A) LENGTH: 21 base pairs
                 (B) TYPE: nucleic acid
                 (C) STRANDEDNESS: single
                 (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:22:

ATCCTCGAGA ACGTTGAATT C                                                    21

(2) INFORMATION FOR SEQ ID NO:23:

(i) SEQUENCE CHARACTERISTICS:
                 (A) LENGTH: 34 base pairs
                 (B) TYPE: nucleic acid
                 (C) STRANDEDNESS: single
                 (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:23:

AATCTAGAAA TAATTTTGTT TAACTTTAAG AAGG                                      34

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:24:

TAGAATTCCA TGGTATATCT CCTTCTTAAA          30

(2) INFORMATION FOR SEQ ID NO:25:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:25:

CCCAAGCTTC TGTTCGTGGT CCGCGTTCTG TTTCTGAAA      39

(2) INFORMATION FOR SEQ ID NO:26:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:26:

GAAACAGAAC GCGGACCACG AACAGAAGCT TGGG         34

(2) INFORMATION FOR SEQ ID NO:27:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:27:

TCCAGCTGAT GCACAACCTG GGTAAACACC TGAACT                36

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:28:

AGGTGTTTAC CCAGGTTGTG CATCAGCTGG ATTTCA                36

(2) INFORMATION FOR SEQ ID NO:29:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:29:

CTATGGAACG TGTTGAATGG CTGCGTAAAA AACTGCA               37

(2) INFORMATION FOR SEQ ID NO:30:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:30:

```
TTTTTTACGC AGCCATTCAA CACGTTCCAT AGAGTTC                              37
```

(2) INFORMATION FOR SEQ ID NO:31:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:31:

```
GGACGTTCAC AACTTCTAAG ATATCCGG                                        28
```

(2) INFORMATION FOR SEQ ID NO:32:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:32:

```
CCGGATATCT TAGAAGTTGT GAACGTCCTG CAG                                  33
```

(2) INFORMATION FOR SEQ ID NO:33:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:33:

```
TCAAAGCTTC TGCCATGGGC GGCCGCGTCG ACCGTGGTCC GCGTTCTGTT TCTGAAATCC     60
AG                                                                    62
```

(2) INFORMATION FOR SEQ ID NO:34:

(i) SEQUENCE CHARACTERISTICS:
        (A) LENGTH: 40 base pairs
        (B) TYPE: nucleic acid

```
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:34:

CTCGATATCT TACTCGAGAG CGCAGAAGTT GTGAACGTCC                           40

(2) INFORMATION FOR SEQ ID NO:35:

(i) SEQUENCE CHARACTERISTICS:
           (A) LENGTH: 14 amino acids
           (B) TYPE: amino acid
           (C) STRANDEDNESS: single
           (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:35:

Phe Val Asn Gly Pro Arg Ala Met Val Asp Asp Asp Asp Lys
 1               5                  10

(2) INFORMATION FOR SEQ ID NO:36:

(i) SEQUENCE CHARACTERISTICS:
           (A) LENGTH: 26 base pairs
           (B) TYPE: nucleic acid
           (C) STRANDEDNESS: single
           (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:36:

GGCAAACACC AGGGACCTGA GCACTG                                         26

(2) INFORMATION FOR SEQ ID NO:37:

(i) SEQUENCE CHARACTERISTICS:
           (A) LENGTH: 30 base pairs
           (B) TYPE: nucleic acid
           (C) STRANDEDNESS: single
           (D) TOPOLOGY: linear (ii) MOLECULE TYPE: Genomic DNA (iii) HYPOTHETICAL: NO (iv) ANTI-SENSE: NO
```

(v) FRAGMENT TYPE:

(vi) ORIGINAL SOURCE:

(xi) SEQUENCE DESCRIPTION: SEQ ID NO:37:

CTGAGGATCC TCAACCAGGG TCATGCTTTC                                    30

(2) INFORMATION FOR SEQ ID NO:38:

(i) SEQUENCE CHARACTERISTICS:
               (A) LENGTH: 26 base pairs
               (B) TYPE: nucleic acid
               (C) STRANDEDNESS: single
               (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:38:

CTTAACTTCA ATGCGGAGGG TGAACC                                        26

(2) INFORMATION FOR SEQ ID NO:39:

(i) SEQUENCE CHARACTERISTICS:
               (A) LENGTH: 41 base pairs
               (B) TYPE: nucleic acid
               (C) STRANDEDNESS: single
               (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:39:

TGCTGCAGGA CATCATGTCC CGTCAGCAGG GTGAATCTAA C                       41

(2) INFORMATION FOR SEQ ID NO:40:

(i) SEQUENCE CHARACTERISTICS:
               (A) LENGTH: 50 base pairs
               (B) TYPE: nucleic acid
               (C) STRANDEDNESS: single
               (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:40:

CCGAATTCGA TATCTTACTC GAGCATAGCG CACAGACGAG CACGAGCACC              50

(2) INFORMATION FOR SEQ ID NO:41:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:41:

CAAAGCTTTC GCCATGGTCG ACGACGACGA CAAATACGCT GACGCTATCT TCACCAACTC        60

T                                                                      61

(2) INFORMATION FOR SEQ ID NO:42:

(i) SEQUENCE CHARACTERISTICS:
            (A) LENGTH: 60 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:42:

GTCCTGCAGC AGTTTACGAG CAGACAGCTG ACCCAGAACT TTACGGTAAG AGTTGGTGAA        60

(2) INFORMATION FOR SEQ ID NO:43:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:43:

CCAAAGCTTT CGGTGGTGGT GGTGGTCCGC GTGGT                                  35

(2) INFORMATION FOR SEQ ID NO:44:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: Genomic DNA

```
    (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:44:

GTCGTCGACC ATGGCGCAAC CACGCGGACC                                         30

(2) INFORMATION FOR SEQ ID NO:45:

(i) SEQUENCE CHARACTERISTICS:
          (A) LENGTH: 51 base pairs
          (B) TYPE: nucleic acid
          (C) STRANDEDNESS: single
          (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:45:

GTCAAATTTG GCGGCCGCGG TGGTGGTGGT GGTGTTAACG GTCCGCGTGG T                 51

(2) INFORMATION FOR SEQ ID NO:46:

(i) SEQUENCE CHARACTERISTICS:
          (A) LENGTH: 52 base pairs
          (B) TYPE: nucleic acid
          (C) STRANDEDNESS: single
          (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:46:

GTCCTCGAGG GTACCTTCAG CATGCATGTC GACAGCGCAA CCACGCGGAC CG                52

(2) INFORMATION FOR SEQ ID NO:47:

(i) SEQUENCE CHARACTERISTICS:
          (A) LENGTH: 60 base pairs
          (B) TYPE: nucleic acid
          (C) STRANDEDNESS: single
          (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:47:
```

```
CTGGGTACCT TCACCTCCGA CGTTTCCTCC TACCTGGAAG GTCAGGCTGC TAAAGAATTC          60
```

(2) INFORMATION FOR SEQ ID NO:48:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:48:

```
CCTGGTCGAC TTACTCGAGA GCGCAACGAC CTTTAACCAG CCAAGCGATG AATTCTTTAG          60
C                                                                         61
```

(2) INFORMATION FOR SEQ ID NO:49:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:49:

```
AGGCGCCATG GTCGGCGGCG GCGACATGCA TGCTGAAGG                                 39
```

(2) INFORMATION FOR SEQ ID NO:50:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: Genomic DNA (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:50:

```
CCTGGTCGAC TTACTCGAGA GCGCAACGAC CTTTAACCAG CCAAGCGATG AATTCTTTAG          60
C                                                                         61
```

(2) INFORMATION FOR SEQ ID NO:51:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:51:

His Asp Glu Phe Glu Arg His Ala Glu Gly Thr Phe Thr Ser Asp Val
 1               5                  10                  15

Ser Ser Tyr Leu Glu Gly Gln Ala Ala Lys Glu Phe Ile Ala Trp Leu
            20                  25                  30

Val Lys Gly Arg
        35

(2) INFORMATION FOR SEQ ID NO:52:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:52:

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly
            20                  25

(2) INFORMATION FOR SEQ ID NO:53:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:53:

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg

```
            20                  25                  30
```

(2) INFORMATION FOR SEQ ID NO:54:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:54:

```
His Asp Glu Phe Glu Arg His Ala Glu Gly Thr Phe Thr Ser Asp Val
1               5                  10                  15

Ser Ser Tyr Leu Glu Gly Gln Ala Ala Lys Glu Phe Ile Ala Trp Leu
            20                  25                  30

Val Lys Gly Xaa
        35
```

(2) INFORMATION FOR SEQ ID NO:55:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:55:

```
Ala Met His Ala Glu Gly Thr Phe Thr Ser Asp Val Ser Ser Tyr Leu
1               5                  10                  15

Glu Gly Gln Ala Ala Lys Glu Phe Ile Ala Trp Leu Val Lys Gly Arg
            20                  25                  30

Cys
```

(2) INFORMATION FOR SEQ ID NO:56:

(i) SEQUENCE CHARACTERISTICS:
        (A) LENGTH: 34 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:56:

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
                20                  25                  30

Asn Phe (2) INFORMATION FOR SEQ ID NO:57:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:57:

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
                20                  25                  30

Glu Ser Asn Gln Glu Arg Gly Ala Arg Ala Arg Leu
        35                  40

(2) INFORMATION FOR SEQ ID NO:58:

(i) SEQUENCE CHARACTERISTICS:
        (A) LENGTH: 49 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:58:

Asp Asp Asp Asp Lys Tyr Ala Asp Ala Ile Phe Thr Asn Ser Tyr Arg
1               5                   10                  15

Lys Val Leu Gly Gln Leu Ser Ala Arg Lys Leu Leu Gln Asp Ile Met
                20                  25                  30

Ser Arg Gln Gln Gly Glu Ser Asn Gln Glu Arg Gly Ala Arg Ala Arg
        35                  40                  45

Leu (2) INFORMATION FOR SEQ ID NO:59:

(i) SEQUENCE CHARACTERISTICS:
        (A) LENGTH: 6 amino acids
        (B) TYPE: amino acid (C) STRANDEDNESS: single
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:59:

Gly Cys Ala Val Asp Met
1               5

(2) INFORMATION FOR SEQ ID NO:60:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:60:

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Met
            20                  25                  30

(2) INFORMATION FOR SEQ ID NO:61:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:61:

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Xaa
            20                  25                  30

(2) INFORMATION FOR SEQ ID NO:62:

(i) SEQUENCE CHARACTERISTICS:
        (A) LENGTH: 30 amino acids
        (B) TYPE: amino acid
        (C) STRANDEDNESS: single

```
            (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:62:

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Met
            20                  25                  30

(2) INFORMATION FOR SEQ ID NO:63:

(i) SEQUENCE CHARACTERISTICS:
         (A) LENGTH: 32 amino acids
         (B) TYPE: amino acid
         (C) STRANDEDNESS: single
         (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:

(xi) SEQUENCE DESCRIPTION: SEQ ID NO:63:

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Cys Ala
            20                  25                  30
```